United States Patent
Warren et al.

(10) Patent No.: US 8,265,737 B2
(45) Date of Patent: Sep. 11, 2012

(54) METHODS AND DEVICES FOR IDENTIFYING OVERDETECTION OF CARDIAC SIGNALS

(75) Inventors: Jay A. Warren, San Juan Capistrano, CA (US); Venugopal Allavatam, Oceanside, CA (US); Rick Sanghera, San Clemente, CA (US); Surekha Palreddy, Maplewood, MN (US)

(73) Assignee: Cameron Health, Inc., San Clemente, CA (US)

( * ) Notice: Subject to any disclaimer, the term of this patent is extended or adjusted under 35 U.S.C. 154(b) by 38 days.

(21) Appl. No.: 12/913,642

(22) Filed: Oct. 27, 2010

(65) Prior Publication Data

US 2011/0098585 A1    Apr. 28, 2011

Related U.S. Application Data

(60) Provisional application No. 61/255,249, filed on Oct. 27, 2009.

(51) Int. Cl.
*A61B 5/04* (2006.01)
*A61B 5/02* (2006.01)
*A61N 1/00* (2006.01)

(52) U.S. Cl. ........... 600/509; 600/508; 600/518; 607/27

(58) Field of Classification Search .................. 609/508, 609/509, 518; 607/27; 600/508, 509, 518
See application file for complete search history.

(56) References Cited

U.S. PATENT DOCUMENTS

| | | | |
|---|---|---|---|
| 4,184,493 A | 1/1980 | Langer et al. |
| 4,300,567 A | 11/1981 | Kolenik et al. |
| 4,407,288 A | 10/1983 | Langer et al. |
| 4,450,527 A | 5/1984 | Sramek |
| 4,457,315 A | 7/1984 | Bennish |
| 4,595,009 A | 6/1986 | Leinders |
| 4,679,144 A | 7/1987 | Cox et al. |
| 4,693,253 A | 9/1987 | Adams |
| 4,750,494 A | 6/1988 | King |
| 4,779,617 A | 10/1988 | Whigham |
| 4,979,110 A | 12/1990 | Albrecht et al. |
| 4,989,602 A | 2/1991 | Sholder et al. |
| 5,000,189 A | 3/1991 | Throne et al. |

(Continued)

FOREIGN PATENT DOCUMENTS

EP    0554208 A2    8/1993

OTHER PUBLICATIONS

Gunderson et al., "An Algorithm to Predict Implantable Cardioverter-Defibrillator Lead Failure," JACC, Nov. 2004, vol. 44, No. 9, pp. 1898-1902.

(Continued)

*Primary Examiner* — Niketa Patel
*Assistant Examiner* — William Levicky
(74) *Attorney, Agent, or Firm* — Pramudji Law Group PLLC; Ari Pramudji; Mark Schroeder

(57) ABSTRACT

Methods, systems, and devices for signal analysis in an implanted cardiac monitoring and treatment device such as an implantable cardioverter defibrillator. In illustrative examples, sensed data including detected events is analyzed to identify likely overdetection of cardiac events. In some illustrative examples, when overdetection is identified, data may be modified to correct for overdetection, to reduce the impact of overdetection, or to ignore overdetected data.

27 Claims, 12 Drawing Sheets

U.S. PATENT DOCUMENTS

| | | |
|---|---|---|
| 5,105,810 A | 4/1992 | Collins et al. |
| 5,184,616 A | 2/1993 | Weiss |
| 5,193,535 A | 3/1993 | Bardy et al. |
| 5,215,098 A | 6/1993 | Steinhaus et al. |
| 5,217,021 A | 6/1993 | Steinhaus et al. |
| 5,271,411 A | 12/1993 | Ripley et al. |
| 5,280,792 A | 1/1994 | Leong et al. |
| 5,299,119 A | 3/1994 | Kraf et al. |
| 5,313,953 A | 5/1994 | Yomtov et al. |
| 5,331,966 A | 7/1994 | Bennett et al. |
| 5,342,402 A | 8/1994 | Olson et al. |
| 5,342,407 A | 8/1994 | Dahl et al. |
| 5,351,696 A | 10/1994 | Riff et al. |
| 5,376,104 A | 12/1994 | Sakai et al. |
| 5,423,326 A | 6/1995 | Wang et al. |
| 5,486,199 A | 1/1996 | Kim et al. |
| 5,522,852 A | 6/1996 | White et al. |
| 5,534,019 A | 7/1996 | Paspa |
| 5,545,186 A | 8/1996 | Olson et al. |
| 5,558,098 A | 9/1996 | Fain |
| 5,607,455 A | 3/1997 | Armstrong |
| 5,658,317 A | 8/1997 | Haefner et al. |
| 5,709,215 A | 1/1998 | Perttu et al. |
| 5,776,168 A | 7/1998 | Gunderson |
| 5,817,134 A | 10/1998 | Greenhut et al. |
| 5,827,197 A | 10/1998 | Bocek et al. |
| 5,857,977 A | 1/1999 | Caswell et al. |
| 5,991,657 A | 11/1999 | Kim |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Grey |
| 6,148,230 A | 11/2000 | KenKnight |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,334,071 B1 | 12/2001 | Lu |
| 6,377,844 B1 | 4/2002 | Graen |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,449,503 B1 | 9/2002 | Hsu |
| 6,493,579 B1 | 12/2002 | Gilkerson et al. |
| 6,493,584 B1 | 12/2002 | Lu |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 | 9/2003 | McClure et al. |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sarker et al. |
| 7,085,599 B2 | 8/2006 | Kim et al. |
| 7,117,035 B2 | 10/2006 | Wagner et al. |
| 7,149,575 B2 | 12/2006 | Ostroff et al. |
| 7,162,301 B2 | 1/2007 | Kim et al. |
| 7,167,747 B2 * | 1/2007 | Gunderson et al. ................ 607/9 |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson |
| 7,302,294 B2 | 11/2007 | Kamath et al. |
| 7,330,757 B2 | 2/2008 | Ostroff et al. |
| 7,346,392 B2 | 3/2008 | KenKnight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,797,036 B2 | 9/2010 | Zhang et al. |
| 7,801,594 B1 | 9/2010 | Higham |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |
| 2004/0215239 A1 | 10/2004 | Favet et al. |
| 2004/0215240 A1 | 10/2004 | Lovett et al. |
| 2004/0220628 A1 | 11/2004 | Wagner |
| 2004/0230229 A1 | 11/2004 | Lovett et al. |
| 2005/0107838 A1 | 5/2005 | Lovett et al. |
| 2005/0131464 A1 | 6/2005 | Heinrich et al. |
| 2005/0154421 A1 | 7/2005 | Ousdigian |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0235476 A1 | 10/2006 | Gunderson |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | Kenknight |
| 2007/0142736 A1 | 6/2007 | Cazares et al. |
| 2007/0156190 A1 | 7/2007 | Cinbis et al. |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |

| | | |
|---|---|---|
| 2007/0232945 A1 | 10/2007 | Kleckner et al. |
| 2007/0232948 A1 | 10/2007 | Stadler et al. |
| 2007/0233198 A1 | 10/2007 | Ghanem et al. |
| 2007/0239051 A1* | 10/2007 | Ghanem et al. ............... 600/512 |
| 2007/0276445 A1 | 11/2007 | Sanghera et al. |
| 2008/0015647 A1 | 1/2008 | Palreddy et al. |
| 2008/0077030 A1 | 3/2008 | Ostroff et al. |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |
| 2008/0172098 A1 | 7/2008 | Gunderson |
| 2008/0183085 A1 | 7/2008 | Van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy et al. |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2009/0036788 A1 | 2/2009 | Nabutovsky et al. |
| 2009/0043352 A1 | 2/2009 | Brooke et al. |
| 2009/0054796 A1 | 2/2009 | Sanghera et al. |
| 2009/0054938 A1 | 2/2009 | Ostroff et al. |
| 2009/0093731 A1 | 4/2009 | Palreddy et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0187227 A1 | 7/2009 | Palreddy et al. |
| 2009/0228057 A1 | 9/2009 | Allavatam et al. |
| 2009/0240157 A1 | 9/2009 | Liam et al. |
| 2009/0240300 A1 | 9/2009 | Liam et al. |
| 2009/0259271 A1 | 10/2009 | Allavatam et al. |
| 2010/0004713 A1 | 1/2010 | Warren et al. |
| 2010/0094369 A1 | 4/2010 | Allavatam et al. |
| 2010/0152798 A1 | 6/2010 | Sanghera et al. |
| 2010/0152799 A1 | 6/2010 | Sanghera et al. |
| 2010/0331904 A1 | 12/2010 | Warren et al. |
| 2011/0098775 A1 | 4/2011 | Allavatam et al. |

OTHER PUBLICATIONS

Olson et al., "Onset and Stability for Ventricular Tachyarrhythmia Detection in an Implantable Pacer-Cardioverter-Defibrillator," IEEE, (1987) pp. 167-170.

Schuder, "The Role of an Engineering Oriented Medical Research Group in Developing Improved Methods and Devices for Achieving Ventricular Defibrillation: The University of Missouri Experience," PACE, vol. 16, Jan. 1993, pp. 95-124.

Schwake et al., "Komplikationen nit Sonden bei 340 Patienten mit einem Implantierbaren Kardioverter/Defibrillator," Z Kardiol (1999)vol. 88, No. 8 pp. 559-565.

Swerdlow, et al., "Advanced ICD Troubleshooting: Part I," online article at http://www.medscape.com/viewarticle/520588_print, accessed and printed Jul. 7, 2009, indicates publication Jan. 9, 2006 (publication date not confirmed).

Throne, "A Comparison of Four New Time-Domain Techniques for Discriminating Monomorphic Ventricular Tachycardia from Sinus Rhythm Using Ventricular Waveform Morphology," IEEE Transactions on Biomedical Engineering, vol. 38, No. 6, Jun. 1991, pp. 561-570.

Warren et al., Methods and Devices that Identify Overdetection in Implantable Cardiac Systems, U.S. Appl. No. 61/375,732, filed Aug. 20, 2010.

* cited by examiner

METHODS AND DEVICES FOR IDENTIFYING OVERDETECTION OF CARDIAC SIGNALS

RELATED APPLICATIONS

The present application claims the benefit of and priority to U.S. Provisional Patent Application No. 61/255,249, titled METHODS AND DEVICES FOR IDENTIFYING OVERDETECTION OF CARDIAC SIGNALS, and filed 27 Oct. 2009. The present application is also related to the following US Patent Applications, and the disclosure of each is incorporated herein by reference:

U.S. patent application Ser. No. 12/355,552, published as US Patent Application Publication Number 2009-0187227, which claims the benefit of U.S. Provisional Patent Application No. 61/022,265;

U.S. patent application Ser. No. 12/399,901, published as US Patent Application Publication Number 2009-0228057, which claims the benefit of U.S. Provisional Patent Application No. 61/034,938;

U.S. patent application Ser. No. 12/399,914, published as US Patent Application Publication Number 2009-0259271, which claims the benefit of U.S. Provisional Patent Application Nos. 61/034,938 and 61/051,332;

U.S. patent application Ser. No. 12/437,547, published as US Patent Application Publication Number 2010-0004713, which also claims the benefit of U.S. Provisional Patent Application No. 61/051,332; and U.S. Provisional Patent Application No. 61/221,316, filed 29 Jun. 2009.

FIELD

The present invention relates generally to implantable medical device systems that sense and analyze cardiac signals. More particularly, the present invention relates to implantable medical devices that sense signals within an implantee's body in order to classify cardiac activity as likely benign or malignant.

BACKGROUND

Implantable cardiac devices typically sense cardiac electrical signals in an implantee and classify the implantee's cardiac rhythm as normal/benign or malignant. Illustrative malignant rhythms may include ventricular fibrillation and/or polymorphic ventricular tachyarrhythmia. The accuracy with which an implantable medical device analyzes sensed signals determines how well it makes therapy determinations and other decisions.

New and/or alternative methods and devices for cardiac signal analysis are desired.

SUMMARY

Various illustrative embodiments of the present invention are directed toward improved accuracy in cardiac signal analysis by implantable medical devices. Some illustrative embodiments identify overdetection of cardiac events. Some illustrative embodiments also correct at least some detection data and use the corrected data to make operational decisions. The invention may be embodied in methods, devices and/or systems.

DETAILED DESCRIPTION

Figure 1:
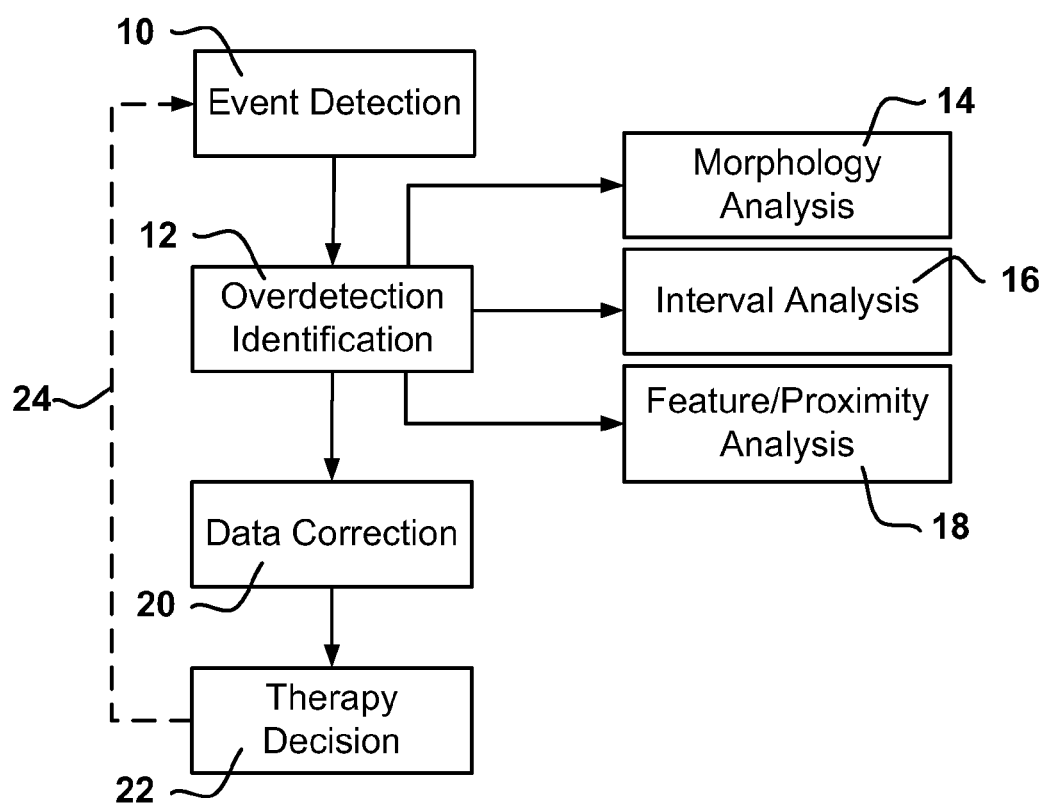
FIG. 1 is a block diagram for an illustrative method of identifying overdetection and taking corrective action.

The following detailed description should be read with reference to the drawings. The drawings, which are not necessarily to scale, depict illustrative embodiments and are not intended to limit the scope of the invention.

The nomenclature used herein indicates that a signal is sensed by an implantable cardiac device system, events are detected in the sensed signal, and cardiac rhythms are classified by use of the detected events (detections). Rhythm classification includes the identification of malignant rhythms, such as ventricular fibrillation or certain tachyarrhythmias, for example. Implantable therapy systems make therapy/stimulus decisions in reliance upon the classification of the cardiac rhythm.

When detecting events, an implantable cardiac device may compare the sensed signal to a detection threshold. For example, if the sensed signal crosses the detection threshold, a new detected event is declared. The detection threshold may have a shape defined by a detection profile, and may be static or ever changing, depending upon the system configuration.

A cardiac electrogram includes several portions (often referenced as "waves") and, according to well known convention, these are labeled with letters including P, Q, R, S, and T, each of which corresponds to particular physiological events. Each cardiac cycle generally has several, if not all, of these portions, though not all are visible on any given electrogram. It is typical to design detection algorithms, and detection profiles, to detect the R-wave or QRS complex. However, any repeatably detectable segment or portion of the cardiac cycle may be used for detection.

For purposes of ascertaining beat rate cardiac cycle should be counted in a repeatable manner so that one detected event is declared for each cardiac cycle. Overdetection (such as a double or triple detection) may occur if a device or method declares more than one detected event within a single cardiac cycle. Examples include the detection of both an R-wave and a trailing T-wave as well as multiple detections of a QRS complex. Those skilled in the art understand that detection accuracy in cardiac devices can be challenged by any number of variations of "normal" cardiac activity. For example, a P-wave may be detected and followed by detection of a trailing part of the QRS or a T-wave from the same cardiac cycle. Overdetection may also occur if noise causes an event to be declared when no cardiac event has taken place, for example, due to external therapy or noise, pacing or motion artifact, non-cardiac muscle noise, etc.

Overdetection can lead to overcounting of cardiac cycles. For example, if one cardiac cycle takes place and a device declares multiple detected events, overdetection has occurred. If the beat rate is then calculated by using each of these detections, overcounting occurs. For example, detected events are separated by intervals and these intervals can be used to generate an average interval, which can then be used to calculate rate. Extra detections will shorten the length of the intervals, making for an inflated rate calculation.

Overcounting in reliance on overdetected events can result in erroneously high rate calculation. Miscalculation of heart rate can lead to incorrect rhythm classification and therapy decisions, because calculated heart rates may be used alone or in combination with other factors to classify cardiac rhythms as treatable or not treatable. Some embodiments are directed at identifying overdetection and/or correcting data that results from overdetection.

Several embodiments are directed at identifying overdetections and/or possible overdetections. These methods lead to marking of suspect events or overdetected events, as needed. In the context presented herein, suspect events are events that are unreliable and may or may not represent true cardiac events; data relating to a suspect event, including intervals surrounding suspect events, may be omitted from use in analyzing rate. In contrast, an overdetection is recognized by embodiments herein as being reliable, though incorrect. As a result, when an overdetection adjacent to true detections is identified, the intervals around the overdetected event can be combined to generate a longer interval that can be used in rate calculations. Other ameliorative actions can be taken as well, for example, by reusing a previous rate or other calculation, by omitting multiple detection data or by assuming a rate value when overdetection is identified by inserting a predetermined value into the interval calculation. In another example, a first detection method is used until overdetection is identified, and then a second detection method, that reanalyzes sensed data can be implemented. In one example, several detection profile shapes can be stored and introduced into analysis after overdetection is identified, in order to identify a detection profile shape that avoids the identified overdetection.

Detected events in an illustrative framework are categorized into three groups—suspect events, overdetected events, and certified events. Suspect events are considered unreliable, and the suspect events and intervals around suspect events can be discarded and not used in other analysis or rhythm classification steps, such as rate calculation. Overdetected events are considered reliable but incorrectly detected, and intervals around overdetected events are combined together to create longer, combined intervals. Detected events that are neither suspect nor overdetected become certified cardiac events once other analysis for suspect and overdetected events is completed without marking as either suspect or overdetected. Other frameworks can be used instead, for example omitting the concept of suspect events and/or omitting the use of corrected data after overdetection is identified.

Several methods described herein are directed at parsing detected events into certified cardiac events, overdetected events, and suspect events. FIG. 1 shows one example of this overall framework.

Figure 2:
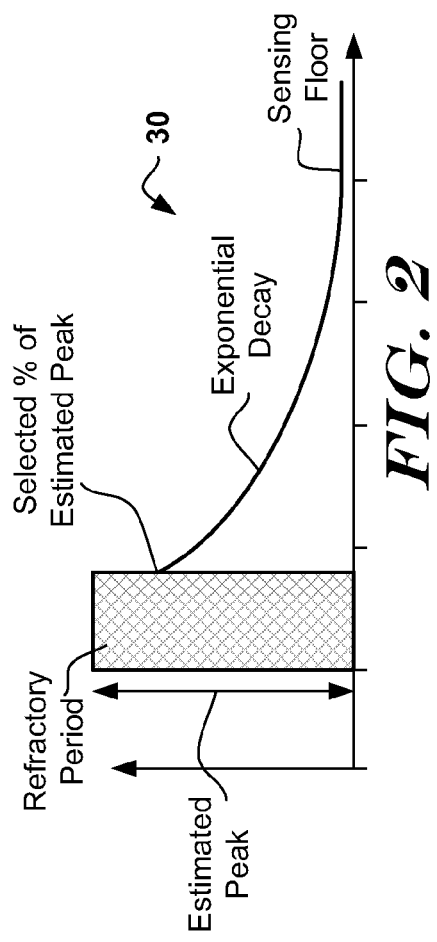
FIG. 2 is an illustration of a detection profile that may be used while detecting cardiac events in an implantable medical device.
Figure 3:
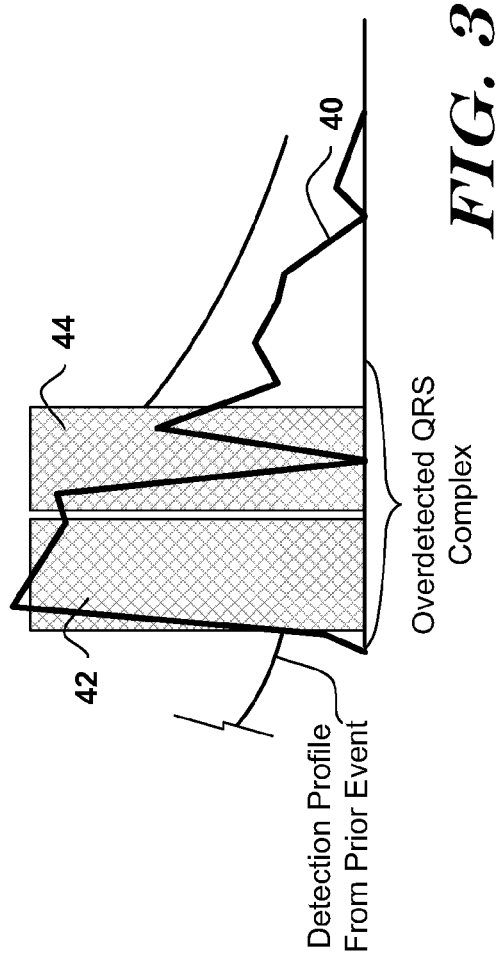
FIG. 3 is a graphical illustration of overdetection of a QRS complex.

FIG. 1 is a block diagram for an illustrative method of identifying overdetection and taking corrective action. The illustrative method begins with event detection 10, where the received cardiac signal is sensed and compared to a detection threshold until the received signal crosses the detection threshold, resulting in declaration of a detected event. FIGS. 2-3 provide illustration of detection step 10. Other forms of event detection could be used instead, for example by observing slew rate to identify periods of high slew rate suggestive of a QRS complex.

Next, the method performs an overdetection identification step 12. This may include one or more of several analysis methods including, as illustratively shown, morphology analysis 14, interval analysis 16 and event and feature/proximity analysis 18. For example, morphology analysis 14 may consider details of the shapes of detected events. Interval analysis 16 may consider the intervals between detected events. Event and feature/proximity analysis may consider combinations of shape and timing characteristics. The methods 14, 16 and 18 may be used separately, in pairs, or as a combination of all three. Several examples of analysis that may be used in steps 14, 16 and/or 18 are shown in U.S. patent application Ser. No. 12/399,914 and/or U.S. patent application Ser. No. 12/437,547, the disclosures of which are incorporated herein by reference. Additional analysis for double detection using width analysis can also be found in U.S. Provisional Patent Application No. 61/375,732, the disclosure of which is incorporated herein by reference.

The event and feature proximity analysis includes combinations of factors. For example, event analysis may look at timing between the starting and/or ending points of detected events. Feature/proximity analysis may look at timing between particular features of detected events, such as zero crossings, amplitude peaks or troughs, inflection points or slew peaks. This may look at features in a single detection, or at features in two adjacent detections, or even at features across three or more detections. Feature/proximity analysis may consider any suitable registration point for analysis, for example, using phase or other relationships between events or detections on different channels of a system, using peaks for a suitable filter transformation (such as a Fourier filter function). Feature/proximity analysis may observe feature timing for registration points in multiple vectors for one or several detected events. While event and feature/proximity analysis are shown combined together at block 18, these may be considered separately as well.

Following overdetection identification 12, if one or more overdetected events are identified, the illustrative embodiment corrects data, as shown at 20. If no data correction is needed at step 20, the method may simply go to the next step, 22. Finally, the method includes a therapy decision, as shown at 22. A therapy decision 22 may classify a cardiac rhythm of the implantee, with emphasis on whether therapy is indicated and/or can improve the implantee's condition. The method iterates to event detection 10, as indicated by line 24. The return to event detection 10 by line 24 may also occur from blocks 12 and 20, though these links are not shown. Therapy decision 22 may observe characteristics across a larger set of 10-30 (or more or less) detected events, using X-out-of-Y counting and/or persistence factors. Some illustrative factors and combinations of factors that may be considered are discussed in U.S. Pat. No. 6,754,528, entitled APPARATUS AND METHOD OF ARRHYTHMIA DETECTION IN A SUBCUTANEOUS IMPLANTABLE CARDIOVERTER/ DEFIBRILLATOR, and U.S. Pat. No. 7,330,757 entitled METHOD FOR DISCRIMINATING BETWEEN VENTRICULAR AND SUPRAVENTRICULAR ARRHYTHMIAS, US Patent Application Publication Number 2006/0167503 titled METHOD FOR ADAPTING CHARGE INITIATION FOR AN IMPLANTABLE CARDIOVERTER-DEFIBRILLATOR, the disclosures of which are incorporated herein by reference. Other methods may be used as a part of the therapy decision 22. In addition, once an initial therapy decision it made, analysis may continue until therapy is delivered, for example as discussed in U.S. Provisional Patent Application No. 61/221,316, the disclosure of which is incorporated herein by reference.

The method of FIG. 1 includes overdetection identification 12 and data correction 20. These steps are designed to improve the accuracy of classification outcomes. Data correction 20 provides one type of ameliorative action that can be undertaken in response to positive identification of overdetection; in another example, sensing configuration changes may be implemented by, for example, changing filtering or gain settings, modifying detection profile characteristics, or changing sensing vector selection. The examples below provide details for implementing these steps in some illustrative embodiments.

FIG. 2 shows an illustrative detection profile 30. The detection profile 30 includes a refractory period. A refractory period, as used herein, indicates a duration of time during which new detected events are not declared. The refractory period is followed by an exponential decay that starts at a selected percentage of an "estimated peak" and decays to the sensing floor. The "estimated peak" is an estimate of the peak signal amplitude for recent detected events, and may be calculated using one or more previously detected events. For example, an average of peak signal amplitudes for previously detected events can be calculated. Other calculations can be used instead. In some instances, if overdetection occurs, the estimated peak can be lowered if the overdetected events peaks have lower amplitude than the peaks of the intended cardiac event features. This may cause further overdetection to occur, as the detection profile becomes more sensitive to lower amplitudes. Thus, in some systems, overdetection can be self-perpetuating.

Following the refractory period, any crossing of the amplitude threshold defined by the detection profile 30 results in a new detected event. The specifics of the detection profile shape can vary widely, and may include, for example and in addition to that which is shown, constant threshold periods, multiple decay periods, increases of the detection profile, etc. In one example, the refractory period is determined in response to rate, with a longer refractory used at lower rates and a shorter refractory period used at higher rates. Ranges for the refractory period may be from about 50 to about 400 milliseconds, with longer and shorter periods usable as well. In one example, a fast-rate refractory period is set in the range of about 80-180 milliseconds or, in a further example, at about 160 milliseconds. Continuing the example, a slow rate refractory period is set in the range of about 160-270 milliseconds, or, in one embodiment, to about 200 milliseconds. Other values or ranges may be used. Further, the detection profile after refractory may include constant threshold time periods, multiple decays, etc. Some examples of detection profiles are also shown in U.S. patent application Ser. No. 12/399,901, the disclosure of which is incorporated herein by reference.

FIG. 3 shows overdetection of a QRS complex. The signal shown at 40 includes a wide elevated amplitude portion that results in two closely spaced detections represented by refractory periods shown in cross hatching at 42 and 44. Due to the width of elevated signal 40, the second detection occurs almost immediately after the end of the first refractory period 42. If left uncorrected, this overdetection could result in erroneously high rate estimates and, possibly, to inappropriate therapy delivery FIG. 4 graphically illustrates two rule sets 50, 52 that can be applied to sets of detected events to identify likely overdetections as part of an event and feature/proximity analysis. For this example, the early and late amplitude peaks in the refractory periods for the detected events are the features for analyzed in a feature/proximity rule. The first rule set 50 is applied to a series of detections [n], [n−1], and [n−2]. A refractory period is shown at 54, having a most-positive peak "A" and a most-negative peak "B", associated with detection [n−2]. From a terminology perspective, peak A is the early peak and peak B is the late peak for refractory period 54. Those skilled in the art will recognize the numerous ways a most-positive and least-negative peak may be described; for example, with a signal that is entirely on the positive side of the isoelectric line during refractory and having a greatest peak at +200 mV and a least trough at +20 mV, the +200 mV peak would be the most-positive peak and the +20 mV peak would be the most negative peak.

The first rule set is illustrated at 50 and considers two timing rules, a first rule that looks at an interval between two signal features, and a second rule that looks at an interval between a signal feature and a detection. Two intervals, T1 and T2 are defined as shown: T1 is the interval between the late peak of detection [n−1] and the detection profile crossing that starts the refractory period of detection [n]; and T2 is the interval between the early peak of detection [n−1] and the late peak of detection [n−2]. If T1 is less than a first threshold and T2 is less than a second threshold, the first rule set is met. As noted above numerous other combinations of features can be used, for example, using various registration points including inflection points, transformation peaks, multi-vector analysis peaks, valleys, zeros, etc. The second rule set at 52 shows another manner of analysis in which a feature/proximity rule integrates a non-timing, shape-based rule (polarity).

The second rule set is illustrated at 52 and considers a timing rule and a feature sequence. The second rule set is applied to a series of detections [m], [m−1], and [m−2]. The timing rule uses T1 as before with rule set 50. The feature sequence calls for alternating peak polarities, wherein the peak polarity of a detection is determined by which of the most-positive peak and most negative peak occurs first in time. If the most-positive peak occurs first, then the detection polarity is positive, and if the most-negative peak occurs first, then the detection polarity is negative. For example, the detection associated with refractory period 56 is considered a positive polarity detection. As shown, detection [m−2] is a positive polarity detection, and detection [m−1] is a negative polarity detection and, therefore, detection [m−2] and detection [m−1] demonstrate alternating polarity. If T1 is less than its associated threshold, then the second rule set is met.

Figure 4:
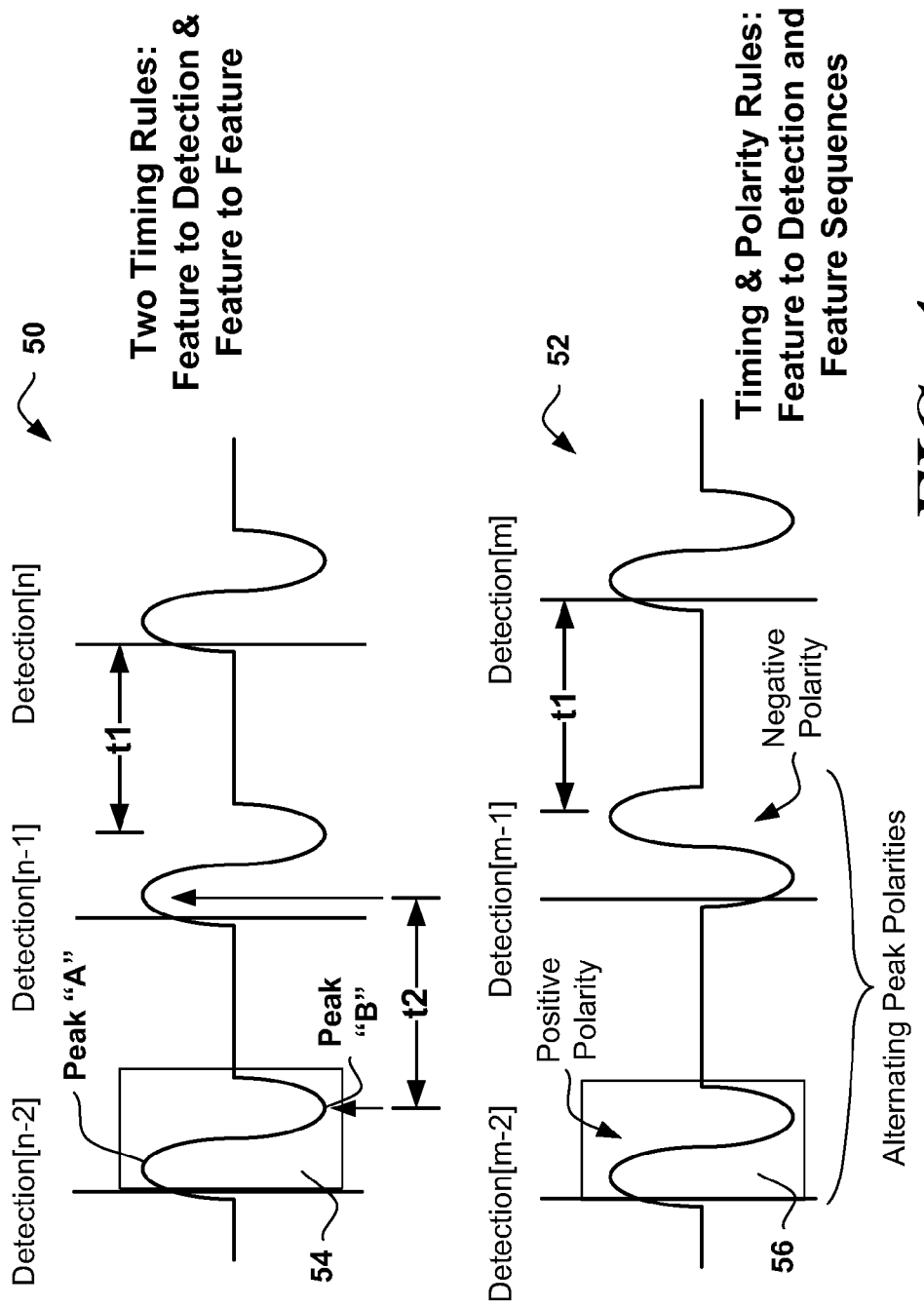
FIG. 4 graphically illustrates two rule sets that can be applied in some illustrative embodiments for identifying overdetection of a QRS complex.
Figure 5:
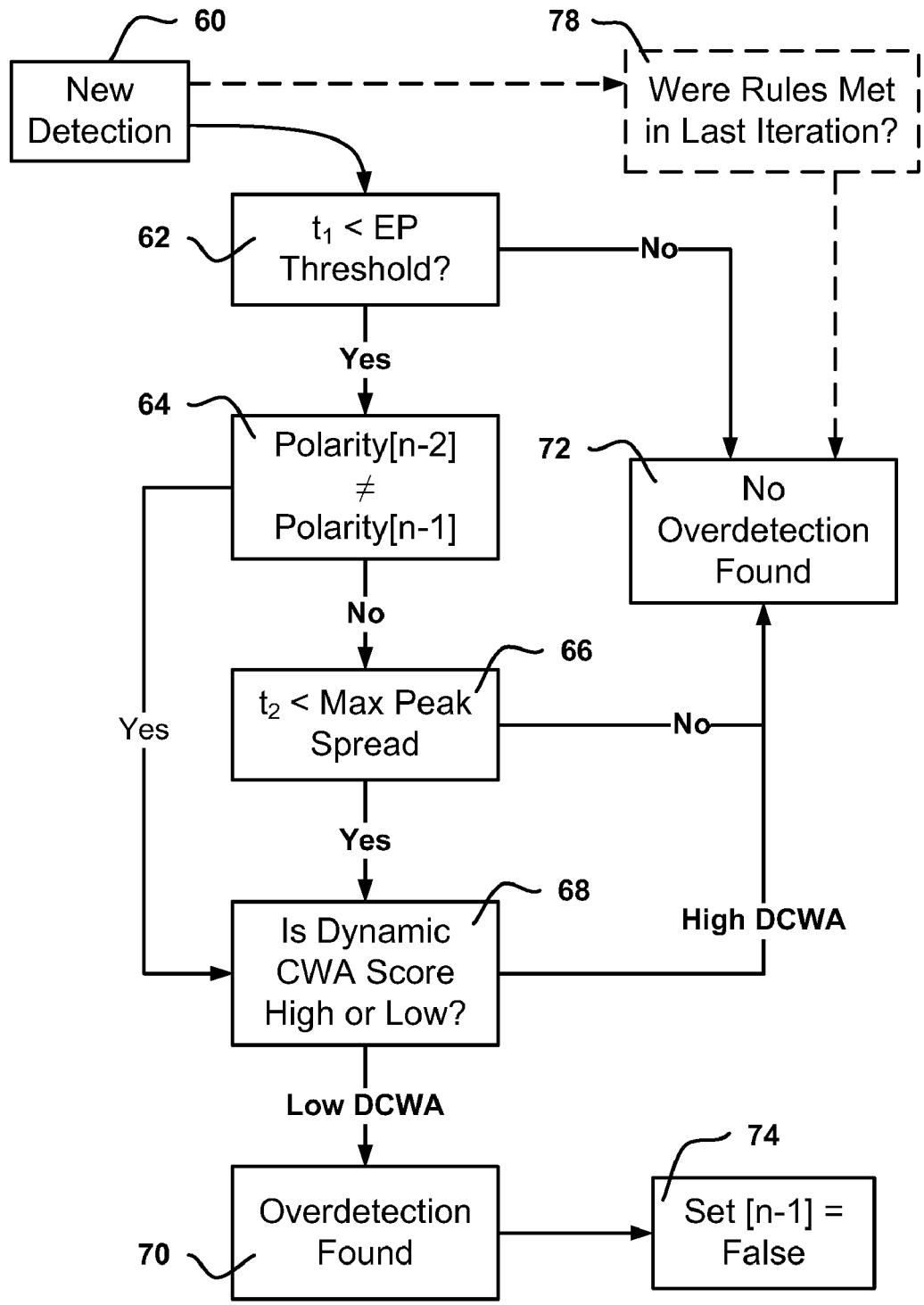
FIG. 5 shows, in a block diagram, a method of identifying overdetection of a QRS complex using the rule sets illustrated in FIG. 4

FIG. 5 shows use of the rule sets from FIG. 4 in a larger method. For purposes of the illustration, the rule sets are applied to a set of events [n], [n−1] and [n−2], and refers to polarity and durations T1 and T2 in a manner similar to FIG. 4. Following a new detection 60, the method determines whether T1 is less than an event proximity threshold (EP Threshold), as shown at 62. In the illustrative example, the EP Threshold can be set to the Template Window Offset, an interval equaling the period between the alignment point of the template and the end of the template window (see FIG. 7, below). In an illustrative example, the Template Window is approximately 160 milliseconds long, and the Template Window Offset may be in the range of 0 to 160 milliseconds. This length of the Template Window can vary as desired. In another example, the EP Threshold may be limited to a range within an available Template Window Offset range, for example, between 40 and 140 milliseconds. In yet another example, the EP Threshold may be set to a percentage of the Template Window length, without relying on the Template Window Offset. In yet another example, the EP Threshold may be set to a fixed value, for example, in the range of about 20 to 200 milliseconds.

If T1 is shorter than the EP Threshold at 62, then the method continues to 64, where it determines whether the polarities of detection [n−1] and detection [n−2] are unequal. If not, then the method continues to block 66 and determines whether T2 is less than a Max Peak Spread threshold. Max Peak Spread may be set to a relatively short duration, for example, in the range of 10-100 milliseconds. This ensures that the rule set will only be met when polarities do not alternate if the sequence of detections occurs with specific peak location features. In an illustrative example, Max Peak Spread is in the range of about 20 milliseconds. In another illustrative example, Max Peak Spread is set to a percentage of the Template Window, where the Template Window may be variable in length.

In still a further example, the template is formed by starting with a wide Template Window and masking early and late portions of the Template Window if the desired portion of the cardiac complex is narrower than the template window. For example, the Template Window may be set to about 160 milliseconds in length and, if the QRS complex that is used to establish the template is about 100 milliseconds long and is centered in the template window following a detection, then masks of 30 milliseconds would be placed at the start and end of the window, with the 100 millisecond template therebetween. In this example, Max Peak Spread is adjusted to account for one of the mask portions, for example, rather than Max Peak Spread of 20 milliseconds, the Max Peak Spread may be the longer of the latter mask and 20 milliseconds, such that Max Peak Spread would be modified in view of the template window masking and set to 30 milliseconds. Max Peak Spread may, in another embodiment, be set as the sum of the latter mask and the 20 milliseconds noted. Other combinations or calculations may be used instead. In yet another example, Max Peak Spread may be scaled up or down based on the overall amplitude of the peaks of the signal, in order to accommodate slew-rate-limits on accurate identification of peaks that could be caused when a high amplitude signal changes quickly. Max Peak Spread may be defined in terms of the number of samples rather than a period of time. The Template Window may be a different length, for example in the range of 60-200 milliseconds, or larger or smaller, and the other variables may also change accordingly.

Figure 9A:
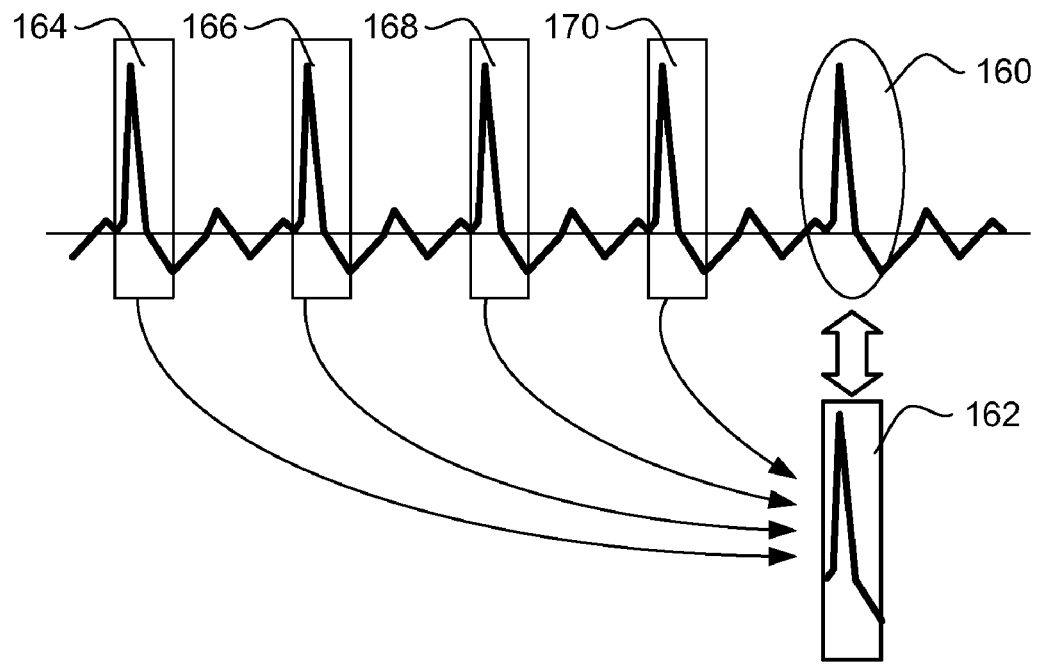
FIGS. 9A-9B illustrate methods of performing a dynamic correlation analysis.
Figure 9B:
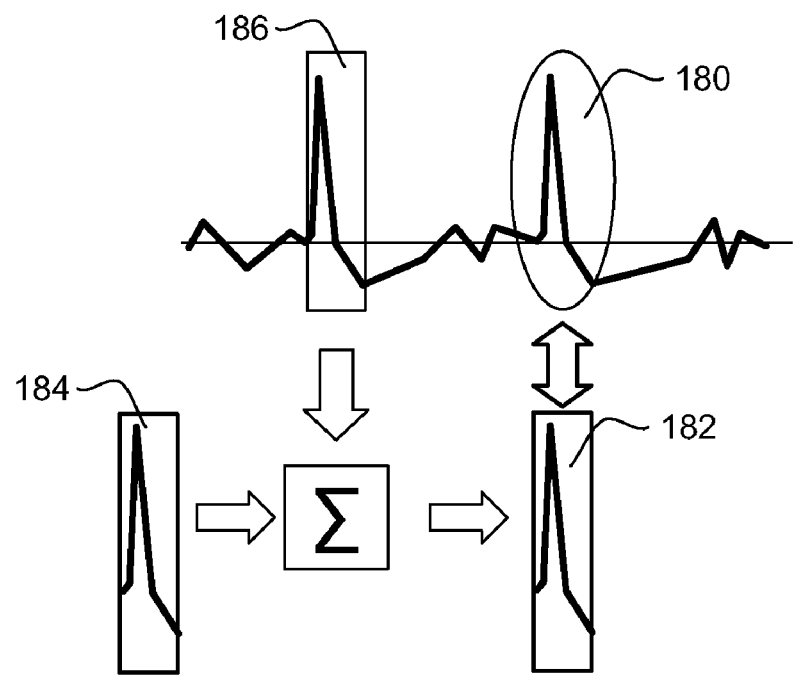

If either of blocks 64 or 66 is satisfied, the method then continues to determining whether detection [n−1] shows high correlation to a template, as shown at 68. In the example shown, a dynamic correlation waveform analysis is performed, using a dynamic template that is related to the morphology of recent events. Some illustrative examples of dynamic templating are shown in FIGS. 9A-9B. If desired, rather than a dynamic correlation score, the method may use a static template correlation score, where the static template is stored in advance. If the correlation is low, then an overdetection is found, as indicated at 72.

In an illustrative example, after overdetection is found, an intermediate set of True or False markings is applied. The True-False marking stores overdetection analysis results for pattern recognition. For example, in some embodiments, False markings are applied to indicate possible overdetection pending identification of an overall pattern that supports a conclusion that overdetection has occurred. If no such pattern is found, the events labeled "False" can be treated as suspect events in which confidence is lacking; if a pattern of overdetection is found, then the "False" events can be treated as overdetections and associated data can be corrected with confidence. The pattern recognition may take place as shown below in FIGS. 10A-10B. Other patterns can be used as well.

Figure 10A:
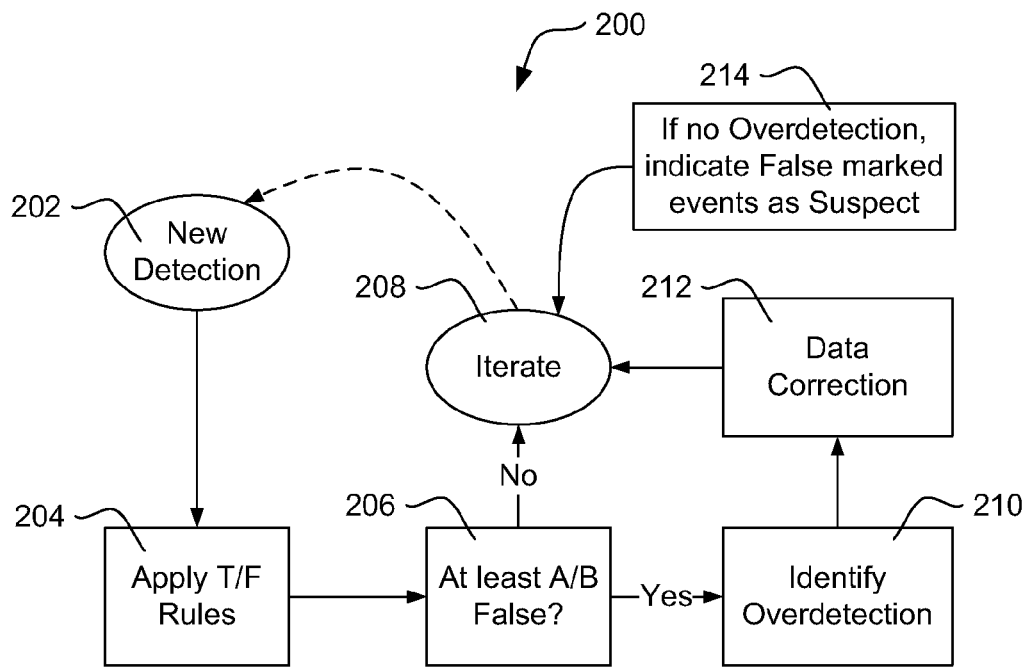
FIG. 10A shows in block diagram form the use of true/false markers on detected events to determine whether data correction should occur.
Figure 10B:
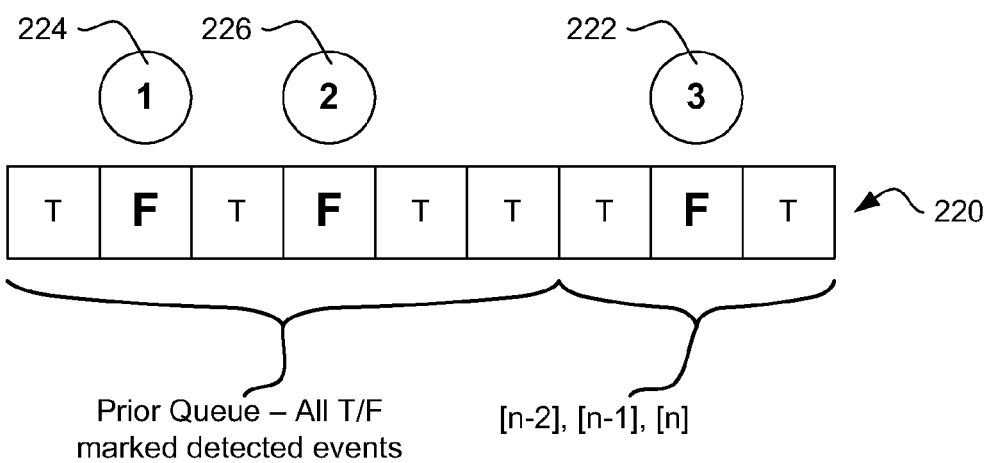
FIG. 10B demonstrates analysis of a set of detected events to determine whether data correction should occur in response to a likely overdetected event.

In the illustrative example, if overdetection is found, as shown at 74, detection [n−1] is labeled false for purposes of the analysis shown in FIGS. 10A-10B. If condition 62 fails, or if both of 64 and 66 fail, the method finds no overdetection, as indicated at 70. Further, if detection [n−1] demonstrates a high correlation at 68, then no overdetection is found as shown at block 70. The correlation score check at 68 is optional, and may be omitted in some examples.

The correlation scoring step at 68 is illustratively shown with a single consideration of the dynamic correlation waveform analysis (DCWA). Repeated overdetection is not likely to result in consistent high DCWA scores, and so the DCWA check at 68 excludes circumstances that are not likely to be the result of overdetection. A system may also check that both DCWA[n−1] and DCWA[n−2] are below a desired threshold before allowing an overdetection to be declared. Testing consecutive detections may add to the assurance that a consistent pattern of poor detection is identified.

In addition, in some systems there may be hardware limitation that could prevent valid completion of a DCWA score during the time period between two detections. For example, in low-power systems, if a number of calculations are needed to perform the correlation analysis and high-power, higher speed circuitry and clocks are not activated to save energy, it is possible that one of the DCWA scores may not be read out in time for analysis. If that is the case, step 68 may be bypassed. Suitable methods of determining whether DCWA has completed may be used, such as setting a flag indicating the calculation is incomplete or checking whether the DCWA readouts are the same for both [n−1] and [n−2], or other methods depending upon the system setup.

In some embodiments, a bypass step is provided as shown at 78. If the prior detection at [n−2] has already been marked as an overdetection, the rules are bypassed such that [n−1] is not marked as an overdetection and the method waits a next iteration. The bypass step 78 avoids marking a string of consecutive events as overdetections. In as method including bypass step 78, at most alternating detected events can be marked as overdetections using the event and feature/proximity analysis. A bypass step 78 may be omitted in other examples.

Figure 6:
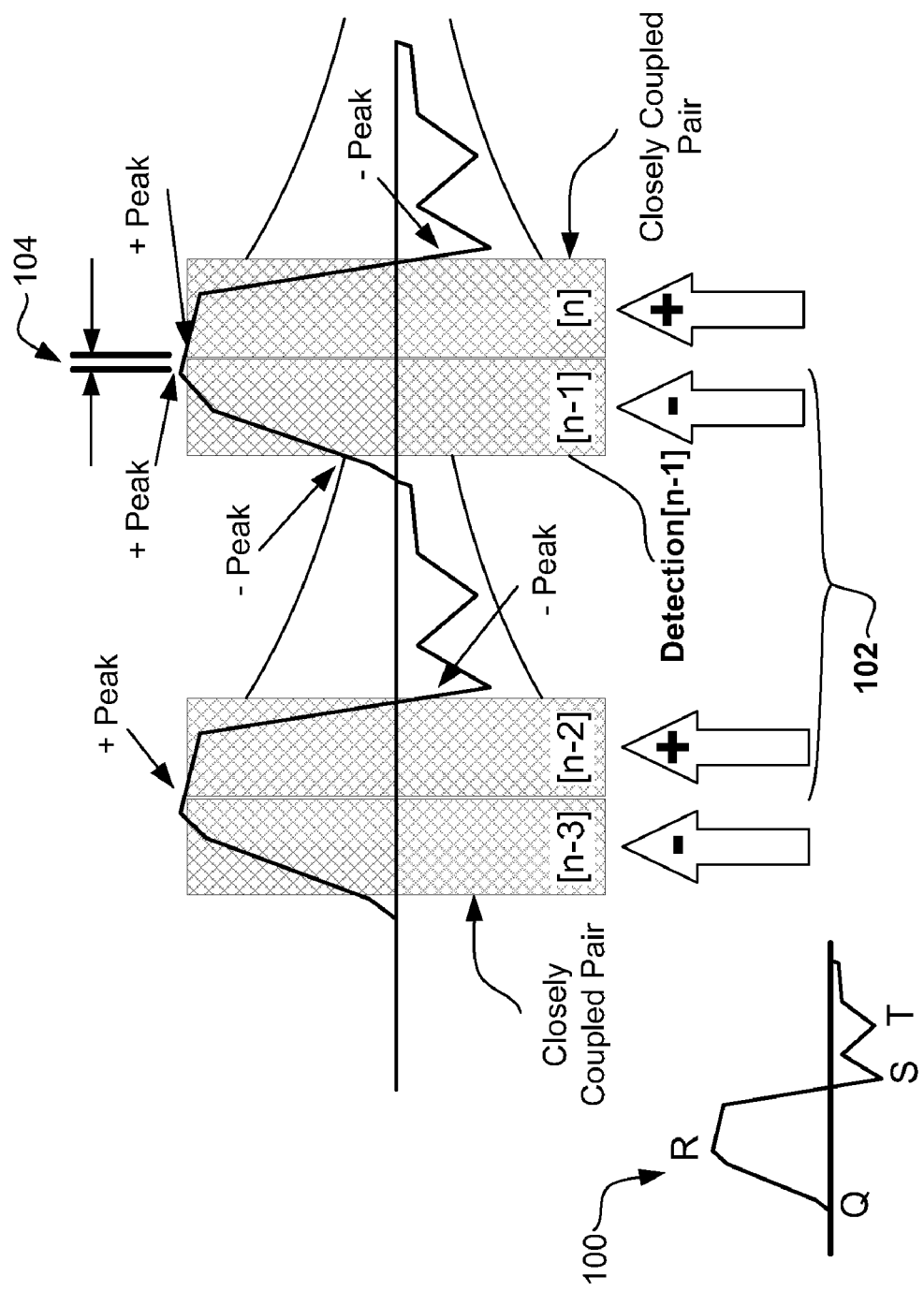
FIG. 6 graphically illustrates application of one of the rule sets of FIGS. 4-5 to an overdetected QRS complex.

Turning now to FIG. 6, one of the rule sets is shown in application to a series of double-detected QRS complexes. The shape of the QRS complex is highlighted at 100. Overdetection can be seen by the close coupling of two refractory periods over each QRS complex. For example, detection [n] immediately follows detection [n−1], and detection [n−2] immediately follows detection [n−3]. That the polarities are alternating from detection [n−2] to detection [n−1] is shown at 102, and the close coupling of the latter peak of detection [n−1] to the start of the refractory period for detection [n] is shown at 104. In view of these features, detection [n−1] is a likely overdetection and is marked as false (see step 74 of FIG. 5).

Figure 7:
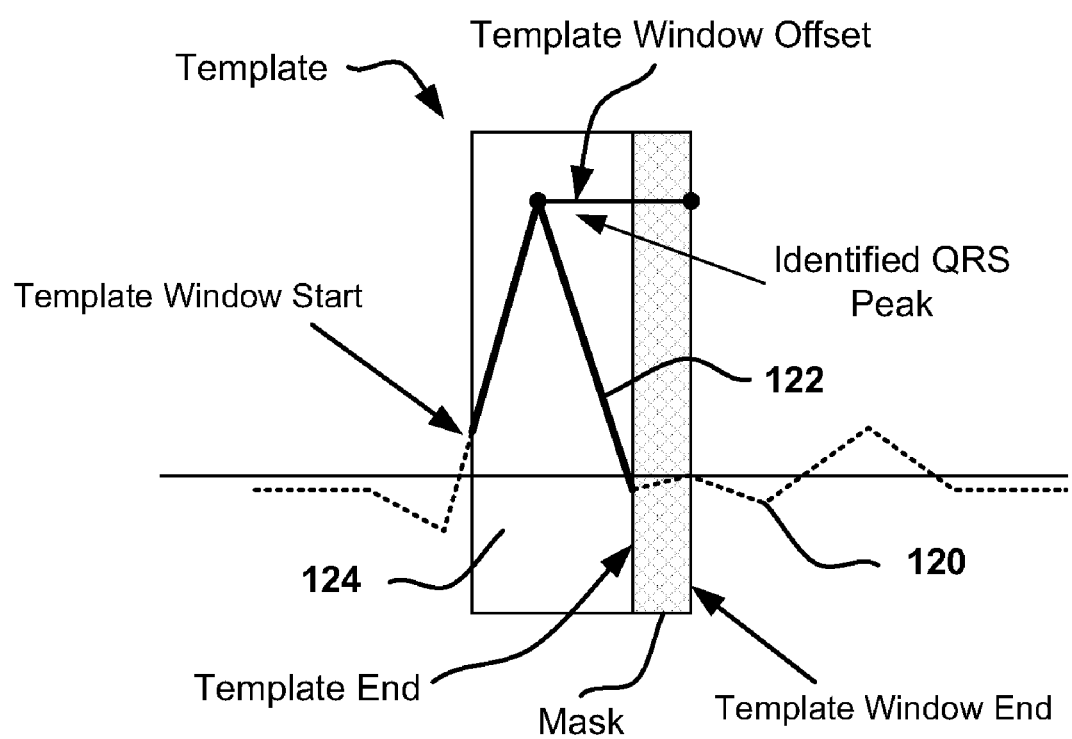
FIG. 7 shows an illustrative basis for setting one of the parameters of one of the rule sets shown in FIGS. 4-5.

FIG. 7 provides an illustration of the Template Window Offset that can be used in analyzing interval T1. In an example, the highest amplitude point in the template is used as an alignment point. When a detected event is to be compared to the template, the highest amplitude point of the detected event is identified and aligned with the template alignment point. A window of data around the template alignment point is compared to corresponding data around the highest amplitude point of the sensed signal. The template window offset is simply a characteristic of the stored template indicated how far the alignment point is located from the rightmost sample (the last-in-time sample) of the template window. This is shown in FIG. 7, where the signal 120 from which the template is created is shown relative to the template data 122 that appears inside the template window 124. The peak of the template data 122 is offset from the right edge of the template window 124 by the Template Window Offset. This provides one example of an interval that can be used for comparison to T1.

The example in FIG. 7 makes the comparison for T1 adaptive to the template for a given system; as noted above, other illustrative embodiments may use a fixed threshold (for example, 20-200 milliseconds). In another example, a different characteristic of the detected signal may be used, for example, the measured template QRS width, or a percentage thereof. In yet a further example, rate may be used to modify the T1 threshold by, for example, reducing T1 in response to higher rate settings. Also, in some examples, the refractory period duration may change in response to rate (shown for example in U.S. patent application Ser. No. 12/399,901), and T1 may be adjusted accordingly. In one illustration, set refractory periods can be used for fast rate (Refractory of about 160 milliseconds) and slow rate (Refractory of about 200 milliseconds), and T1 can be adjusted to compensate for the change in refractory by extending T1 by up to 40 milliseconds for the faster rate analysis. In a further illustration, T1 is extended by about 20 milliseconds when fast refractory is called, compensating only partly for the reduced refractory period. Other adjustments may be made as well.

Figure 8:
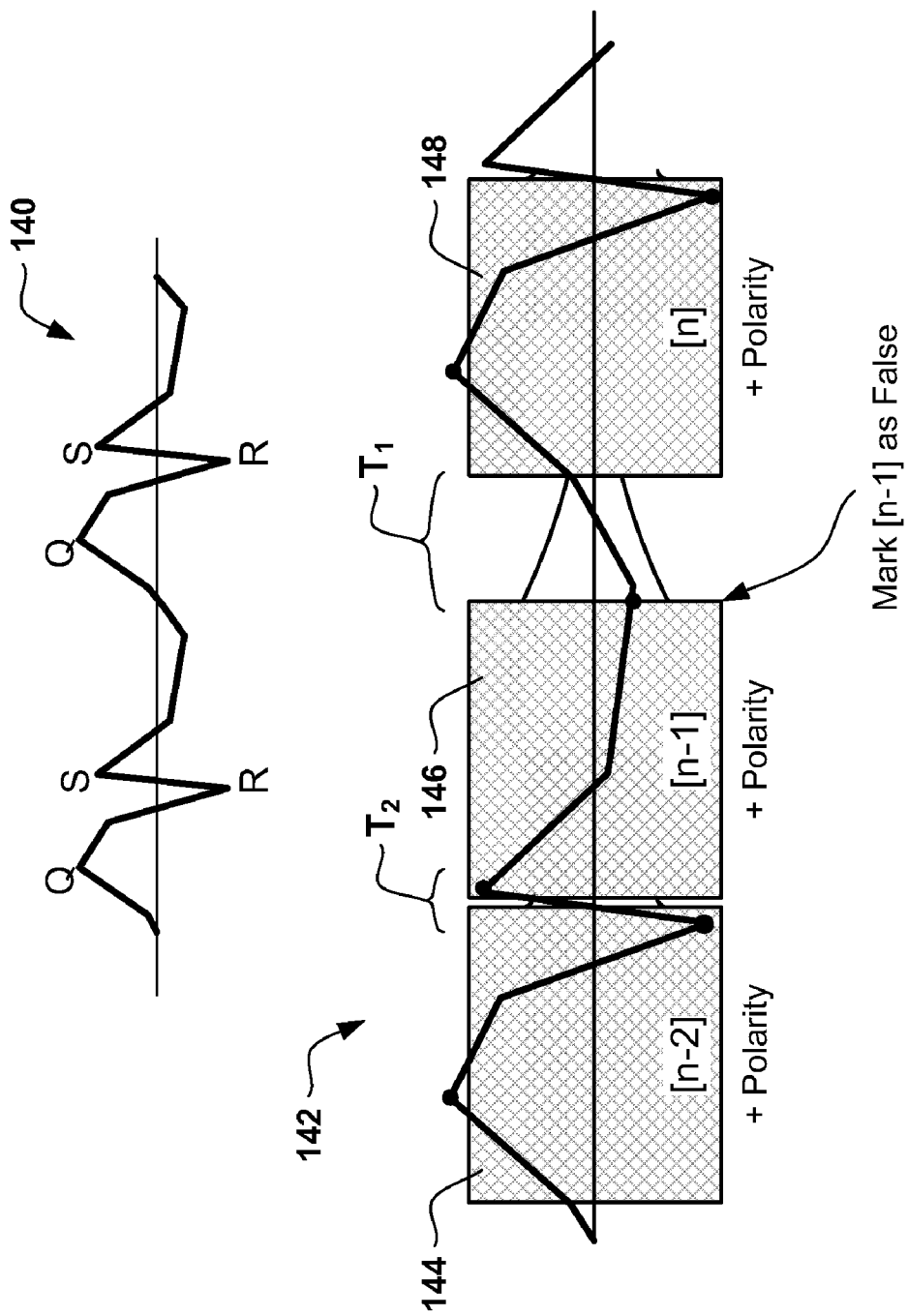
FIG. 8 graphically illustrates application of one of the rule sets of FIGS. 4-5 to an overdetected QRS complex.

FIG. 8 demonstrates the application of another rule set, this time using two timing features as shown at 50 in FIG. 4. The cardiac signal is shown in isolation at 140. As shown at 142, this cardiac signal is detected three times resulting in refractory periods at 144, 146 and 148, associated with detections [n−2], [n−1] and [n]. Each detection shown has positive polarity. Referring to detection [n−1], the early peak is close to the start of refractory period 146. The late peak for detection [n−2] is very near the end of its corresponding refractory period 144. As a result, the two peaks are within the max peak spread interval of one another, meeting the condition for T2. The late peak for detection [n−1] occurs near the end of refractory period 146, and close coupling to detection [n] meets the T1 criteria. This combination would lead detection [n−1] to be marked as false.

FIG. 5 refers to dynamic correlation waveform analysis. FIGS. 9A-9B demonstrate a number of methods of computing a dynamic correlation analysis. In FIG. 9A, dynamic correlation is performed by comparing a newest event 160 to a dynamic template 162 that is formed in any of the following manners:
  as a copy of one of the previous detected events 164, 166, 168, 170;
  as an average of the previous detected events 164, 166, 168, 170;
  as a weighted average of the previous detected events 164, 166, 168, 170, for example, one-half of 170 plus one-fourth of 168 plus one-eighth of each of 166 and 164; or
  as an average of the previous detected events 164, 166, 168, 170 excluding any of the previous detected events 164, 166, 168, 170 did not match the dynamic template 162 when comparison was performed for the given detected event.

Comparison may take the form of a correlation waveform analysis, which may use, for example, one minus the quotient of the area of difference between the template 162 and the scaled detected event 160 divided by the total area under template 162. Other comparisons may be performed, for example wavelet transform analysis, principle component analysis, other signal decompositions or other mathematical functions. For the correlation analysis, the detected event 160 or template 162 may be scaled to match the amplitudes thereof. Scaling may use, for example, the peak amplitude in the event refractory or the average refractory period power, for example. Other scaling factors may be used.

FIG. 9B demonstrates another basis for performing a comparison. In this example, the detected event 180 is compared to a dynamic template 182 that is calculated as the average of the prior dynamic template 184 and the most recent prior detected event 186. The averaging of the prior template and the most recent prior detected event 186 may be a direct sum-and-average, or it may use a weighted approach (⅓ of detected event 186 and ⅔ of the prior dynamic template 184, for example).

Figure 11:
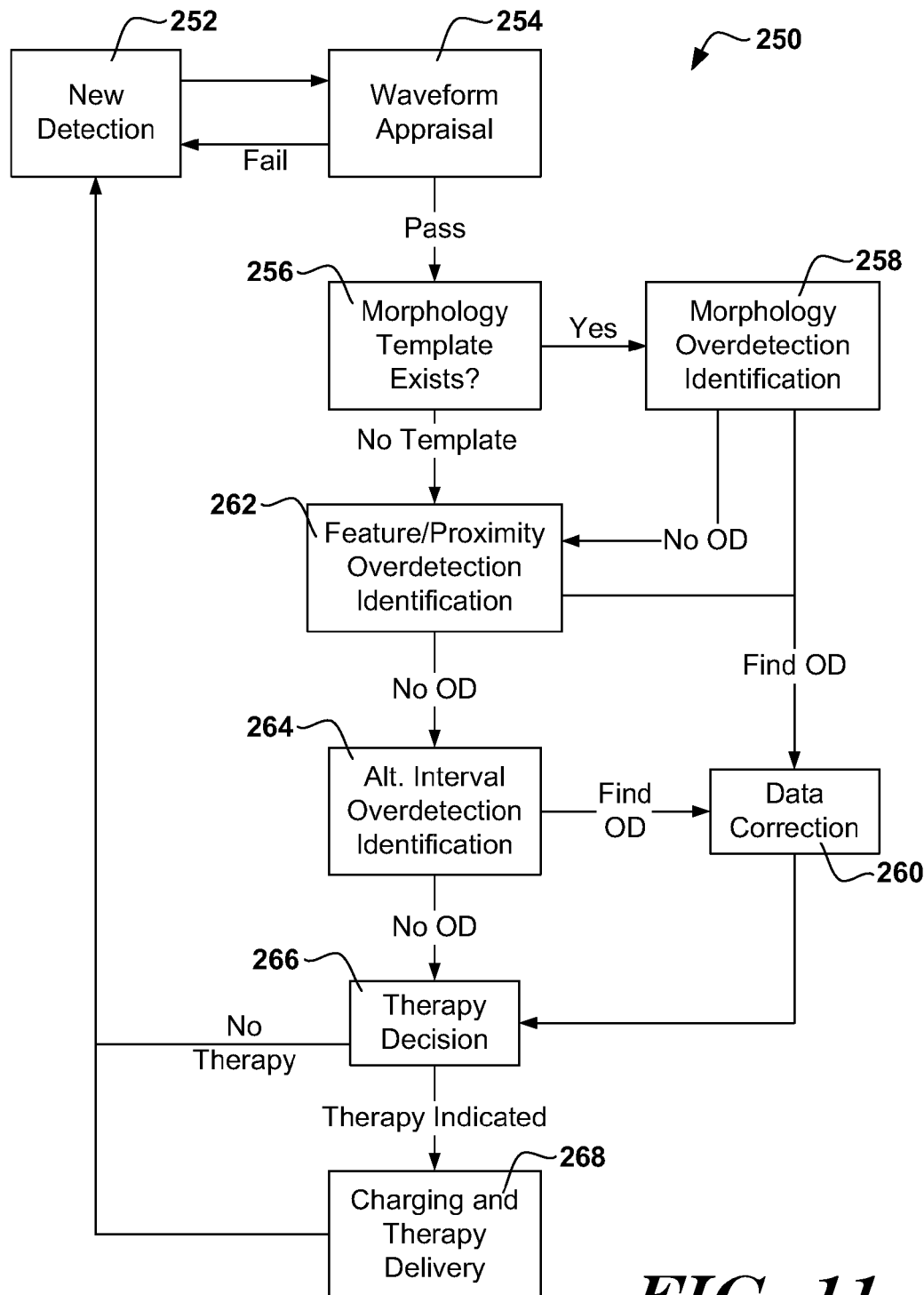
FIG. 11 shows an illustrative example for integration of a waveform appraisal method with multiple overdetection identification methods.

FIGS. 10A-10B demonstrate a manner of determining whether to correct data or discard suspect events as a result of the true-false marking performed as shown in FIGS. 4-8. The method 200 shown in FIG. 10A includes the identification of a new detection at 202, following which the True/False rules are applied at 204 (intermediate steps such as waveform appraisal and/or other overdetection activities are left out for clarity; the method at FIG. 11 shows some of these omitted steps). Next, the method determines whether at least a given ratio, A/B, have been marked false. In one example, NB is read as 3/8; other ratios may be used, as desired. Some examples are 2/6, 3/7, 4/7, 5/9, 7/16. Whether a "majority rule" is applied may depend upon the type of double detection identification methods applied; for example, in some embodiments the True-False marking is limited to half of events—see FIG. 5, bypass step 78, which prevents the rules from being met for consecutive events. If used, such NB criteria may be adaptive to conditions. In one example, an NB condition of 5/9 is used as a default, but once met, the condition is reduced to 3/6 for a period of time such as sixty minutes, since the analysis has already shown a propensity of overdetection. In another example, an A/B condition may vary in response to suspect events being identified for noise purposes, for example by extending the number of events considered or excluding noisy events. In another example, if noise identification prevents detections for a period of time or fails to pass detections to overdetection analysis, then overdetection analysis may not operate, to avoid identifying overdetections from sparse data.

If the NB condition is not met at 206, then the next iteration occurs 208. If the A/B condition is met, then an overdetection is identified as shown at 210. Data correction occurs next, as shown at 212. Some principles of data correction are highlighted in FIG. 12, below. The next iteration is then called, as shown at 208.

As indicated at 214, before proceeding to a next iteration, if the [n−1] detection has been marked False, and no overdetection is identified because the A/B condition is not met, then data with the [n−1] detection is treated as suspect. Again, the treatment of suspect event data is further illustrated in FIG. 12.

Figure 12:
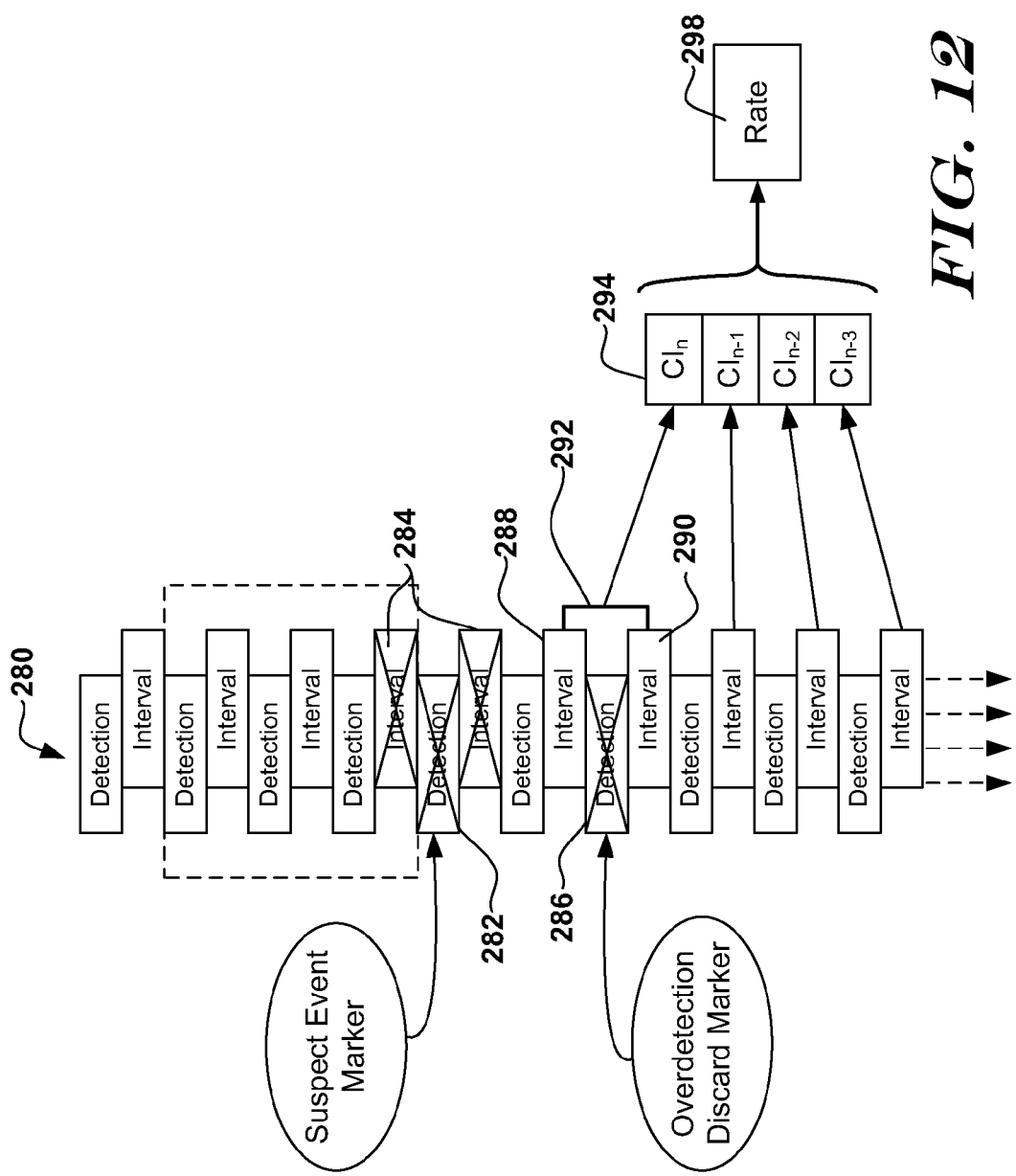
FIG. 12 illustrates how data handling occurs in response to identification of suspect and/or overdetected events.

FIG. 10B illustrates how the steps of FIG. 10A are implemented for a particular sequence of event markers. In the example, a queue of event markers is represented at 220. These include the events indicated as [n], [n−1], [n−2], and a prior queue of events, each of which is marked as either True (T) or False (F). Three detections have been marked false—two in the prior queue, shown at 224 and 226, and a third in the set of [n], [n−1], and [n−2], as shown at 222. For an A/B of 3/8, an overdetection will be marked. In some examples, all three False marked events 222, 224, and 226 would be marked as overdetections. In other examples, only the most recently marked False event—at 222—is marked as an overdetection, such that the method need only reach back through events [n], [n−1] and [n−2] to perform data correction. FIG. 12 shows what can be done with the overdetection marker.

The Ser. No. 12/399,914 application, incorporated by reference above, discusses the use of a pattern identification method as part of the wide QRS overdetection analysis method, with states for the wide QRS method including Out-Of-Range or Off, In-Range Pattern Found, and In-Range Pattern lost, as shown in FIG. 14 thereof, although it is indicated that the in-range and out-of-range features may be omitted, if desired. As an alternative to the pattern analysis shown in FIG. 14 of the Ser. No. 12/399,914 application, FIGS. 10A-10B of the present discussion, below, show the use of a method in which an A-out-of-B rule can be applied to determine whether enough events have met the rule set to justify data correction. The A-out-of-B rule can be applied to the wide QRS methods of the Ser. No. 12/399,914 application, or to the Event and Feature/proximity Analysis shown below. Alternatively, if desired, the pattern analysis in the Ser. No. 12/399,914 application can be used to control the use of a rule set as shown in FIG. 5, below. In another example, larger pattern recognition or the A-out-of-B rule can be omitted, and a rule set for analyzing a single event in the context of adjacent events can be applied.

FIG. 11 illustrates in block diagram form an example of identifying overdetection and making therapy decisions. The illustrative method 250 begins with the declaration of a new detected event, as shown at 252. The detected event undergoes waveform appraisal as indicated at 254. Waveform appraisal 254 analyzes data associated with the detected event to ensure the detection is cardiac in origin. Waveform appraisal can mark detected events having significant noise as suspect events. For example, noise may be identified by counting the number of zero crossings of the signal, or of the first or second derivative of the signal, during a predetermined time period. U.S. Pat. No. 7,248,921, titled METHOD AND DEVICES FOR PERFORMING CARDIAC WAVEFORM APPRAISAL provides additional detailed examples of waveform appraisal 254. Additional examples are shown in U.S. Provisional Patent Application No. 61/255,253, titled ADAPTIVE WAVEFORM APPRAISAL IN AN IMPLANTABLE CARDIAC SYSTEM, filed on even date herewith, and the disclosure of which is incorporated herein by reference.

If the detected event fails waveform appraisal 254, it is marked as a suspect event and the method returns to step 252 and awaits a next detection threshold crossing. Once a detected event is identified that passes waveform appraisal 254, the method 250 goes into steps for analyzing detections and identifying overdetection. As shown at 256, the illustrative method 250 determines whether a morphology template exists. A morphology template is a data set useful for morphological comparison with recently detected event(s). Morphology templates may be formed by implanted device systems or associated programmers, or may be selected or identified by medical personnel. U.S. Pat. No. 7,376,458, entitled METHOD FOR DEFINING SIGNAL TEMPLATES IN IMPLANTABLE CARDIAC DEVICES discusses some examples of template formation and/or testing. In some examples, template formation is performed by identifying a representative QRS complex that is reflective of an average or typical morphology of a cardiac cycle for an implantee, for example, while the implantee is in a resting state or other physiological state.

In an illustrative example of automatic template formation, a detected event is identified and data for the detected event is stored by a device as a preliminary template. In the illustrative example, the preliminary template can be validated by comparing the stored data to stored data for a number of adjacent-in-time detected events. If the set of adjacent-in-time detected events demonstrates high correlation to one another, the preliminary template is validated and a morphology template is defined using the preliminary template. If the preliminary template cannot be validated, it is discarded. Template formation may fail if the sensed signal persistently varies, since high variability may prevent validation of a preliminary template. The query at step 256 determines whether a template is available for use in morphology overdetection identification 258. In some systems, a morphology template will always exist. For example, some embodiments allow a physician to select a representative beat during implantation or during a telemetry session as a morphology template, or a representative template may be selected from a library of known templates. If so, step 256 may be omitted. The morphology overdetection identification 258 may be performed, for example, in accordance with illustrations shown in U.S. patent application Ser. No. 12/399,914, published as US Patent Application Publication Number 2009-0259271, and/or U.S. patent application Ser. No. 12/437,547, published as US Patent Application Publication Number 2010-0004713, each of which is incorporated herein by reference. Some methods include identifying alternating patterns of morphology indicating High-Low-High correlations to the morphology template, wherein the Low correlation events may be marked as overdetections.

If overdetection is found at block 258, the method may advance to data correction indicated at 260. Alternatively, additional overdetection identification steps may be undertaken to provide results from each of several available tools, which may be useful for understanding whether and how the device is performing with each sub-method of overdetection identification. Data correction 260 is further explained below with reference to FIG. 12.

If no overdetection is found at 258, or if no template exists, feature/proximity overdetection identification can be performed, as indicated at 262. This may include the methods shown above in FIGS. 4-8. If desired, the methods described as wide-complex methods in U.S. patent application Ser. No. 12/399,914 may be performed as well. Again, if overdetection is found, the method continues to block 260.

If there is no overdetection found at block 262, the alternating interval overdetection identification 264 is performed. In alternating interval overdetection identification 264, the intervals between detected events are analyzed to determine whether overdetection is occurring. Several illustrative methods for alternating interval overdetection identification are shown in U.S. patent application Ser. No. 12/399,914. Alternating long-short interval combinations may be used to identify likely overdetection. If overdetection is found, again, the method may continue to block 260.

If desired, rate range analysis may be used to select only one of blocks 262, 264 to perform. In the method shown, the two blocks 262 and 264 are both performed regardless of rate.

In another example, a rate limitation may be applied to avoid operating any of the overdetection identification blocks 258, 262, 264 if the detected cardiac rate is too low to present the possibility that an inappropriate shock could be delivered.

Following passage of each overdetection block and/or after data correction 260, a therapy decision is made, as indicated at 266. Therapy indications can be gathered using various methods described in applications and patents referenced herein, including, for example, U.S. patent application Ser. No. 12/399,901, published as US Patent Application Publication Number 2009-0228057, U.S. patent application Ser. No. 12/437,547, published as US Patent Application Publication Number 2010-0004713, U.S. Provisional Patent Application No. 61/221,316, filed 29 Jun. 2009, US Patent Application Publication Number 2006-0167503, and/or U.S. Pat. Nos. 6,754,528 and 7,330,757, the disclosures of which are incorporated herein by reference. If therapy is indicated, then charging and therapy delivery may follow, as indicated at 268. Typically, implantable therapy devices use charging circuitry that takes a period of time to prepare the device for therapy delivery. The method may iterate several times after a charge is initiated before therapy can be delivered, and during such iterations additional analysis may take place, such as that described in US Patent Application Publication Number 2006-0167503 and/or U.S. Provisional Patent Application No. 61/221,316, the disclosures of which are incorporated herein by reference.

FIG. 12 shows how an illustrative system may use suspect event markers and overdetection markers. In the example shown, overdetection markers lead to discarded detected events, and associated intervals are combined together as if the discarded event never took place, at least for purposes of calculating event rate. In the example, the intervals surrounding a suspect event are not combined together and are instead removed from the analysis of rate.

FIG. 12 shows a series of detections separated by intervals at 280. The stream of data is such that the newest detection is on top, and older detections and intervals are shown below. As shown at 282, when a detection receives a suspect event marker, the intervals 284 associated with the suspect event marker are omitted from further analysis.

As shown at 286, when an overdetection discard marker is applied, the interval 288 that follows the overdetection 286 is added to the interval 290 that preceded the overdetection 286. The sum of these intervals 288, 290 (accounting for any refractory period of the detection 286 itself) is combined to form interval 292. The combined interval 292 is passed to a queue of certified intervals shown at 294. Other intervals in the queue will include prior intervals that are not adjacent a suspect event and that have not been combined, as well as any combined intervals. Certified intervals 294 are then used to calculate the rate 296. Additional examples appear in U.S. patent application Ser. No. 12/399,914. The example shown uses four certified intervals 294 to calculate rate 296; a larger or smaller number of intervals may be used to calculate rate 296.

Figure 13:
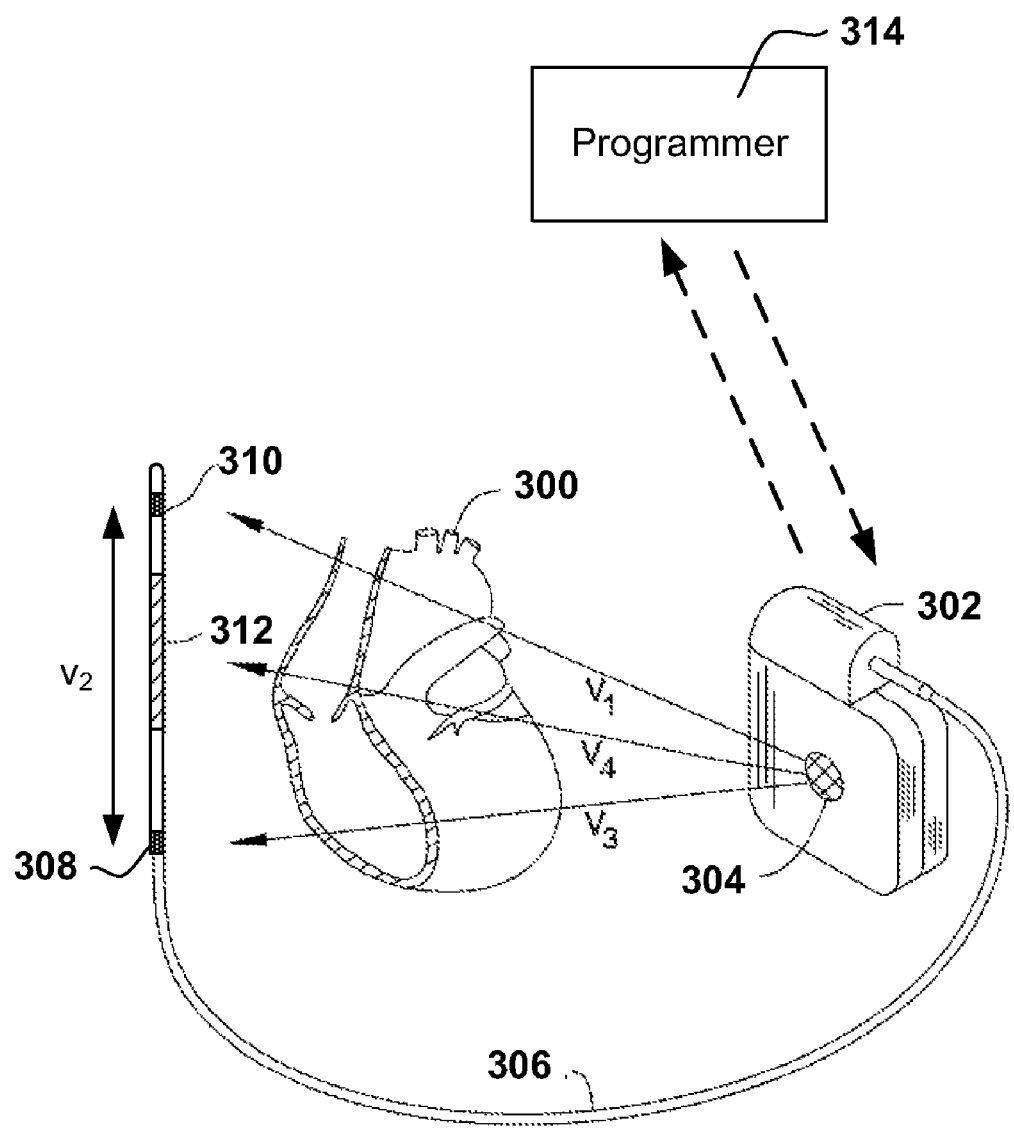
FIG. 13 shows an implantable cardiac stimulus system relative to a patient's heart.

FIG. 13 shows an illustrative implantable medical device and implant location. More particularly, an illustrative subcutaneous-only system is shown in FIG. 13. The subcutaneous system is shown relative to a heart 300, and includes a canister 302 coupled to a lead 306. The canister 302 preferably houses operational circuitry for performing analysis of cardiac activity and for providing a therapy output. The operational circuitry may include batteries, input/output circuitry, power capacitors, a controller, memory, telemetry components, etc., as known in the art.

Electrodes are disposed at locations throughout the system including, for example, an electrode 304 on the canister 302, and electrodes 308, 310, 312 on lead 306. The electrodes 304, 308, 310, 312 may take any suitable form and can be made of any suitable material. For example, the canister electrode 304 may be an isolated button electrode or it may be a region or surface of the canister 302, and the electrodes 308, 310, 312 on lead 306 may be coil electrodes, ring electrodes, or other structures known in the art.

The electrodes 304, 308, 310, 312 define a plurality of sensing vectors such as V1, V2, V3 and, optionally, V4. If desired, one or more vectors V1, V2, V3, and V4 may be chosen as a default sensing vector, for example, as discussed in US Patent Application Publication Number 2007-0276445 titled SYSTEMS AND METHODS FOR SENSING VECTOR SELECTION IN AN IMPLANTABLE MEDICAL DEVICE. Other uses of multiple vectors are shown, for example, in U.S. Pat. No. 7,392,085 titled MULTIPLE ELECTRODE VECTORS FOR IMPLANTABLE CARDIAC TREATMENT DEVICES. Another embodiment considers posture in vector analysis, for example, as discussed in US Patent Application Publication Number 2008-0188901 titled SENSING VECTOR SELECTION IN A CARDIAC STIMULUS DEVICE WITH POSTURAL ASSESSMENT. Multiple sensing vectors may be analyzed, sequentially or in combination, as desired. In one example, sensing vector selection may be modified in response to identification of overdetection as an ameliorative action, particularly if repeated overdetections occur. For example, if 10 overdetections are identified in a 60 second time period, a different sensing vector may be chosen, or vector selection process may be performed.

In another example, the operational circuitry comprises input circuitry for receiving electrical signals from the electrodes 304, 308, 310, 312 and amplifying the received signals according to gain settings controlled by the operational circuitry. In some examples, a gain setting may be changed to address overdetection by, for example, adjusting the response time for automatic gain control to slow or accelerate response to ameliorate positive identification of overdetection, or by toggling between fixed gain and variable/AGC signal processing. The input circuitry may also perform filtering functions, at least some of which may be controlled by the operational circuitry. In yet another example, filtering characteristics can be modified as an ameliorative action, for example, increasing the attenuation of lower frequencies to reduce T-wave amplitudes and/or reducing attenuation to sharpen QRS peaks that may be overdamped and thus wide. In yet another example, characteristics of the detection profile (see for example FIG. 2) can be modified in response to positive identification of overdetection. For example, when overdetection is identified, the refractory period may be extended, or the features of exponential decay can be adjusted. Each of these steps represent ameliorative action in response to positive identification of overdetection.

Therapy may be applied using any chosen pair of electrodes. An illustrative example uses the canister electrode 304 and the coil electrode 312 to apply therapy. Other electrode combinations may be used. Therapy may include mono-, bi- or other multi-phasic cardioversion or defibrillation and/or various pacing operations such as anti-tachycardia pacing (for fast rhythms) and bradycardia pacing (for slow rhythms).

The present invention is not limited to any particular hardware, implant location or configuration. Instead, it is intended as an improvement upon any implantable cardiac system. Some illustrative examples can associate with an external programmer 314 configured to communicate with the implanted device for various purposes, including, for example and without limitation, one or more of the following: device testing; load new/revised software; modify sensing, detection or therapy settings; determine the status of device operation, battery life, or lead integrity; and/or download data relating to the implantee's condition, prior data capture, or treatment. Any suitable communication method may be used, such as various protocols and hardware widely known in the art.

FIG. 13 omits several anatomical landmarks. The illustrative system shown may be implanted beneath the skin outside of the ribcage of the implantee. The location illustratively shown would place the canister 302 at approximately the left axilla of the implantee, level with the cardiac apex, with the lead 306 extending medially toward the xiphoid and then toward the head of the implantee along the left side of the sternum. One illustrative example uses a method/system as shown in commonly assigned US Patent Application Publication Number 2006-0122676 entitled APPARATUS AND METHOD FOR SUBCUTANEOUS ELECTRODE INSERTION, now U.S. Pat. No. 7,655,014. Other illustrative subcutaneous systems and locations are shown in commonly assigned U.S. Pat. Nos. 6,647,292, 6,721,597 and 7,149,575.

The present invention may also be embodied in systems having various implant configurations including, for example, other subcutaneous-only systems, epicardial systems, and/or transvenous systems. The canister 302 may be placed in anterior, lateral, and/or posterior positions including, without limitation, axillary, pectoral, and sub-pectoral positions, as well as placements on either the left or right side of the implantee's torso and/or in the abdomen. Entirely intravascular implantation of the system has also been proposed. The lead 306 may be placed in any of a number of suitable configurations including anterior-posterior combinations, anterior-only combinations, transvenous placement, or other vascular placements.

Unless implicitly required or explicitly stated, the methods below do not require any particular order of steps. It should be understood that when the following examples refer to a "current event," in some embodiments, this means the most recently detected cardiac event is being analyzed. However, this need not be the case, and some embodiments perform analysis that is delayed by one or more detections and or a period of time. Choices shown regarding use of rectified/unrectified signals are merely illustrative, and may be changed if desired. In the illustrative examples that follow, relative comparisons of "greater than" and "less than" can be modified to "greater than or equal to" and "less than or equal to" without changing the underlying concept.

As used herein, "marking an event" indicates that information relating to an event is tracked by any suitable manner. For example, detected events may be stored as individual objects having timestamps, data and a set of characteristics, where "marking" the event indicates modifying the stored characteristics. In another example, various storage buffers may be maintained, wherein entries are made into storage buffers as data analysis occurs, for example, when certain points of the analysis are reached, one or more entries are made in appropriate buffers. The details of the manner in which data is organized can vary widely, and the statement that a detected event or piece of data is "marked" should not be misconstrued as limiting the analysis to any particular manner of preserving such data.

Some examples shown above use four intervals to calculate an average interval, which is then used to calculate cardiac rate. Some other number of intervals may be used, as desired. Any other suitable method of calculating cardiac rate may be used instead.

The completeness of the examples shown is not an indication that all parts are necessary to any given embodiment. Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. An implantable cardiac system (ICS), the ICS comprising operational circuitry coupled to a plurality of implantable electrodes for sensing electric signals, the operational circuitry comprising a controller coupled to memory having an instruction set configuring the ICS to perform a method of cardiac signal analysis comprising:
   sensing signals from the electrodes;
   detecting events in the sensed signals;
   applying event and feature/proximity analysis rules to the detected events to identify overdetection of cardiac signals; and
   identifying overdetection of cardiac signal and performing ameliorative action in response to the identified overdetection;
   wherein the operational circuitry is configured to apply the event and feature/proximity analysis rules across three detected events ([n−2], [n−1], [n]) as follows:
      identifying a late peak in detection [n−2], identifying an early peak and a late peak in detection [n−1] and identifying a detection time for event [n];
      measuring a first interval from the late peak of detection [n−1] to the detection time of event [n] and comparing the first interval to a t1 threshold;
      measuring a second interval from the late peak of detection [n−2] to the early peak of detection [n−1] and comparing the second interval to a t2 threshold; and
      when the first interval is less than the t1 threshold and the second interval is less than the t2 threshold, identifying detection [n−1] as an overdetected event.

2. The ICS of claim 1 wherein:
   the operational circuitry is contained in a canister configured for implantation in the torso of a patient;
   the canister serves as one of the electrodes;
   the ICS further comprises a lead coupled to the canister, the lead including at least two electrodes;
   the operational circuitry is configured to select a default sensing pair from the electrodes on the canister and lead; and
   the ameliorative action comprises performing a vector selection process to determine whether to switch to a different default sensing pair.

3. The ICS of claim 1 wherein the operational circuitry comprises input circuitry for receiving and amplifying signals from the electrodes and the ameliorative action comprises modifying a gain setting of the input circuitry.

4. The ICS of claim 1 wherein the operational circuitry comprises input circuitry for receiving and filtering signals from the electrodes and the ameliorative action comprises modifying a filtering setting of the input circuitry.

5. An implantable cardiac system (ICS), the ICS comprising operational circuitry coupled to a plurality of implantable electrodes for sensing electric signals, the operational circuitry comprising a controller coupled to memory having an instruction set configuring the ICS to perform a method of cardiac signal analysis comprising:

sensing signals from the electrodes;
detecting events in the sensed signals;
applying event and feature/proximity analysis rules to the detected events to identify overdetection of cardiac signals; and
identifying overdetection of cardiac signal and performing ameliorative action in response to the identified overdetection;
wherein the operational circuitry is configured to apply the event and feature/proximity analysis rules across three detected events ([n−2], [n−1], [n]) as follows:
 identifying an early peak and a late peak in detection [n−2], identifying an early peak and a late peak in detection [n−1] and identifying a detection time for event [n];
 measuring a first interval from the late peak of detection [n−1] to the detection time of event [n] and comparing the first interval to a t1 threshold;
 comparing the early peak of the [n−2] detection to the early peak of the [n−1] detection and determining whether the two early peaks alternate polarities; and
 when the first interval is less than the t1 threshold and the early peaks of the [n−2] and [n−1] alternate polarities, identifying detection [n−1] as an overdetected event.

6. The ICS of claim 5 wherein:
the operational circuitry is contained in a canister configured for implantation in the torso of a patient;
the canister serves as one of the electrodes;
the ICS further comprises a lead coupled to the canister, the lead including at least two electrodes;
the operational circuitry is configured to select a default sensing pair from the electrodes on the canister and lead; and
the ameliorative action comprises performing a vector selection process to determine whether to switch to a different default sensing pair.

7. The ICS of claim 5 wherein the operational circuitry comprises input circuitry for receiving and amplifying signals from the electrodes and the ameliorative action comprises modifying a gain setting of the input circuitry.

8. The ICS of claim 5 wherein the operational circuitry comprises input circuitry for receiving and filtering signals from the electrodes and the ameliorative action comprises modifying a filtering setting of the input circuitry.

9. An implantable cardiac system (ICS), the ICS comprising operational circuitry coupled to a plurality of implantable electrodes for sensing electric signals, the operational circuitry comprising a controller coupled to memory having an instruction set configuring the ICS to perform a method of cardiac signal analysis comprising:
 sensing signals from the electrodes;
 detecting events in the sensed signals;
 applying event and feature/proximity analysis rules to the detected events to identify overdetection of cardiac signals; and
 identifying overdetection of cardiac signal and performing ameliorative action in response to the identified overdetection;
 wherein the operational circuitry is configured to apply the event and feature/proximity analysis rules across three detected events ([n−2], [n−1], [n]) as follows:
  identifying an early peak and a late peak in detection [n−2], identifying an early peak and a late peak in detection [n−1] and identifying a detection time for event [n];
  measuring a first interval from the late peak of detection [n−1] to the detection time of event [n] and comparing the first interval to a t1 threshold;
  measuring a second interval from the late peak of detection [n−2] to the early peak of detection [n−1] and comparing the second interval to a t2 threshold;
  comparing the early peak of the [n−2] detection to the early peak of the [n−1] detection and determining whether the two early peaks alternate polarities; and:
   a) when the first interval is less than the t1 threshold and the early peaks of the [n−2] and [n−1] alternate polarities, identifying detection [n−1] as an overdetected event; and
   b) when the first interval is less than the t1 threshold and the second interval is less than the t2 threshold, identifying detection [n−1] as an overdetected event.

10. The ICS of claim 9 wherein:
the operational circuitry is contained in a canister configured for implantation in the torso of a patient;
the canister serves as one of the electrodes;
the ICS further comprises a lead coupled to the canister, the lead including at least two electrodes;
the operational circuitry is configured to select a default sensing pair from the electrodes on the canister and lead; and
the ameliorative action comprises performing a vector selection process to determine whether to switch to a different default sensing pair.

11. The ICS of claim 9 wherein the operational circuitry comprises input circuitry for receiving and amplifying signals from the electrodes and the ameliorative action comprises modifying a gain setting of the input circuitry.

12. The ICS of claim 9 wherein the operational circuitry comprises input circuitry for receiving and filtering signals from the electrodes and the ameliorative action comprises modifying a filtering setting of the input circuitry.

13. An implantable cardiac system (ICS), comprising:
means for sensing signals from an implanted location;
means for detecting events in sensed signals;
means for applying event and feature/proximity analysis rules to detected events to identify overdetection of cardiac signals; and
means for ameliorating overdetection of cardiac signals;
wherein the means for applying event and feature/proximity analysis rules includes a controller configured to apply the event and feature/proximity analysis rules across three detected events ([n−2], [n−1], [n]) as follows:
 identifying a late peak in detection [n−2], identifying an early peak and a late peak in detection [n−1] and identifying a detection time for event [n];
 measuring a first interval from the late peak of detection [n−1] to the detection time of event [n] and comparing the first interval to a t1 threshold;
 measuring a second interval from the late peak of detection [n−2] to the early peak of detection [n−1] and comparing the second interval to a t2 threshold; and
 when the first interval is less than the t1 threshold and the second interval is less than the t2 threshold, identifying detection [n−1] as an overdetected event.

14. The ICS of claim 13 wherein:
the means for sensing signals comprises a plurality of implantable electrodes; and
the means for detecting events in sensed signals comprises a comparing circuit for comparing a received signal to a sensing threshold and, when the sensing threshold is crossed by the received signal, generating an event output.

15. The ICS of claim 14 wherein:
the means for performing ameliorative action comprises switching means for selecting a default sensing pair from among the plurality of implantable electrodes for use in sensing cardiac activity; and
the means for performing ameliorative action is configured to adjust the switching means to modify the default sensing pair in response to identification of overdetected events.

16. The ICS of claim 14 wherein:
the means for performing ameliorative action comprises input circuitry for receiving and amplifying signals from the plurality of implantable electrodes and providing the received and amplified signals to the means for detecting events; and
the means for performing ameliorative action is operative to modify a gain setting of the input circuitry in response to identification of overdetected events.

17. The ICS of claim 14 wherein:
the means for performing ameliorative action comprises input circuitry for receiving and filtering signals from the plurality of implantable electrodes and providing the received and filtered signals to the means for detecting events; and
the means for performing ameliorative action is operative to modify a filtering setting of the input circuitry in response to identification of overdetected events.

18. An implantable cardiac system (ICS), comprising:
means for sensing signals from an implanted location;
means for detecting events in sensed signals;
means for applying event and feature/proximity analysis rules to detected events to identify overdetection of cardiac signals; and
means for ameliorating overdetection of cardiac signals.
wherein the means for applying event and feature/proximity analysis rules includes a controller configured to apply the event and feature/proximity analysis rules across three detected events ([n−2], [n−1], [n]) as follows:
identifying an early peak and a late peak in detection [n−2], identifying an early peak and a late peak in detection [n−1] and identifying a detection time for event [n];
measuring a first interval from the late peak of detection [n−1] to the detection time of event [n] and comparing the first interval to a t1 threshold;
comparing the early peak of the [n−2] detection to the early peak of the [n−1] detection and determining whether the two early peaks alternate polarities;
when the first interval is less than the t1 threshold and the early peaks of the [n−2] and [n−1] alternate polarities, identifying detection [n−1] as an overdetected event.

19. The ICS of claim 18 wherein:
the means for sensing signals comprises a plurality of implantable electrodes; and
the means for detecting events in sensed signals comprises a comparing circuit for comparing a received signal to a sensing threshold and, when the sensing threshold is crossed by the received signal, generating an event output.

20. The ICS of claim 19 wherein:
the means for performing ameliorative action comprises switching means for selecting a default sensing pair from among the plurality of implantable electrodes for use in sensing cardiac activity; and
the means for performing ameliorative action is configured to adjust the switching means to modify the default sensing pair in response to identification of overdetected events.

21. The ICS of claim 19 wherein:
the means for performing ameliorative action comprises input circuitry for receiving and amplifying signals from the plurality of implantable electrodes and providing the received and amplified signals to the means for detecting events; and
the means for performing ameliorative action is operative to modify a gain setting of the input circuitry in response to identification of overdetected events.

22. The ICS of claim 19 wherein:
the means for performing ameliorative action comprises input circuitry for receiving and filtering signals from the plurality of implantable electrodes and providing the received and filtered signals to the means for detecting events; and
the means for performing ameliorative action is operative to modify a filtering setting of the input circuitry in response to identification of overdetected events.

23. An implantable cardiac system (ICS), comprising:
means for sensing signals from an implanted location;
means for detecting events in sensed signals;
means for applying event and feature/proximity analysis rules to detected events to identify overdetection of cardiac signals; and
means for ameliorating overdetection of cardiac signals,
wherein the means for applying event and feature/proximity analysis rules includes a controller configured to apply the event and feature/proximity analysis rules across three detected events ([n−2], [n−1], [n]) as follows:
identifying an early peak and a late peak in detection [n−2], identifying an early peak and a late peak in detection [n−1] and identifying a detection time for event [n];
measuring a first interval from the late peak of detection [n−1] to the detection time of event [n] and comparing the first interval to a t1 threshold;
measuring a second interval from the late peak of detection [n−2] to the early peak of detection [n−1] and comparing the second interval to a t2 threshold;
comparing the early peak of the [n−2] detection to the early peak of the [n−1] detection and determining whether the two early peaks alternate polarities; and:
a) when the first interval is less than the t1 threshold and the early peaks of the [n−2] and [n−1] alternate polarities, identifying detection [n−1] as an overdetected event; and
b) when the first interval is less than the t1 threshold and the second interval is less than the t2 threshold, identifying detection [n−1] as an overdetected event.

24. The ICS of claim 23 wherein:
the means for sensing signals comprises a plurality of implantable electrodes; and
the means for detecting events in sensed signals comprises a comparing circuit for comparing a received signal to a sensing threshold and, when the sensing threshold is crossed by the received signal, generating an event output.

25. The ICS of claim 24 wherein:
the means for performing ameliorative action comprises switching means for selecting a default sensing pair from among the plurality of implantable electrodes for use in sensing cardiac activity; and the means for performing ameliorative action is configured to adjust the switching means to modify the default sensing pair in response to identification of overdetected events.

26. The ICS of claim 24 wherein:

the means for performing ameliorative action comprises input circuitry for receiving and amplifying signals from the plurality of implantable electrodes and providing the received and amplified signals to the means for detecting events; and the means for performing ameliorative action is operative to modify a gain setting of the input circuitry in response to identification of overdetected events.

27. The ICS of claim 24 wherein:

the means for performing ameliorative action comprises input circuitry for receiving and filtering signals from the plurality of implantable electrodes and providing the received and filtered signals to the means for detecting events; and the means for performing ameliorative action is operative to modify a filtering setting of the input circuitry in response to identification of overdetected events.

* * * * *